United States Patent [19]

Ito et al.

[11] Patent Number: 5,216,608
[45] Date of Patent: Jun. 1, 1993

[54] APPARATUS AND A METHOD FOR ESTIMATING THE FRICTION COEFFICIENT OF A ROAD SURFACE AND CONTROLLING A DRIVING CONDITION OF A VEHICLE IN ACCORDANCE WITH THE ESTIMATED FRICTION COEFFICIENT

[75] Inventors: Masayoshi Ito, Okazaki; Kiichi Yamada, Nagoya; Masayuki Hashiguchi, Ohbu; Keiji Isoda, Nagoya; Toshio Shigehara, Okazaki, all of Japan

[73] Assignee: Mitsubishi Jidosha Kogyo Kabushiki Kaisha, Tokyo, Japan

[21] Appl. No.: 644,251

[22] Filed: Jan. 22, 1991

[30] Foreign Application Priority Data

| Jan. 25, 1990 | [JP] | Japan | 2-13553 |
| Jan. 30, 1990 | [JP] | Japan | 2-17821 |
| Jan. 30, 1990 | [JP] | Japan | 2-17829 |
| Jan. 30, 1990 | [JP] | Japan | 2-17830 |
| Jan. 30, 1990 | [JP] | Japan | 2-17839 |
| May 16, 1990 | [JP] | Japan | 2-124281 |
| May 16, 1990 | [JP] | Japan | 2-124282 |
| May 16, 1990 | [JP] | Japan | 2-124290 |
| May 16, 1990 | [JP] | Japan | 2-124293 |

[51] Int. Cl.$^5$ .............................................. B60K 26/00
[52] U.S. Cl. ........................ 364/426.03; 364/426.01; 180/197
[58] Field of Search ............. 364/426.01, 426.02, 364/426.03; 180/197, 249, 248; 303/15, 97, 100, 103

[56] References Cited

U.S. PATENT DOCUMENTS

| 3,538,742 | 10/1968 | Benning | 73/9 |
| 3,893,330 | 7/1975 | Shute et al. | 73/9 |
| 4,212,063 | 7/1980 | Härdmark | 364/426.01 |
| 4,315,426 | 2/1982 | Brandon | 73/9 |
| 4,594,878 | 6/1986 | Abe et al. | 73/9 |
| 4,637,487 | 1/1987 | Nakamura et al. | 180/197 |
| 4,669,569 | 6/1987 | Suzuki et al. | 180/249 |
| 4,779,447 | 10/1988 | Rath | 73/9 |
| 4,794,539 | 12/1988 | Wallentowitz et al. | 364/426.01 |
| 4,825,367 | 4/1989 | Nagaoka et al. | 364/426.03 X |
| 4,841,446 | 6/1989 | Leiber et al. | 364/426.02 |
| 4,855,917 | 8/1989 | Sawano et al. | 364/426.02 |
| 4,933,857 | 6/1990 | Hashiguchi et al. | 364/426.02 |
| 4,976,330 | 12/1990 | Matsumoto | 180/197 |
| 4,998,593 | 3/1991 | Karnopp et al. | 364/426.02 X |
| 5,005,132 | 4/1991 | Yoshino | 364/426.02 |
| 5,015,041 | 5/1991 | Kuwana et al. | 364/426.02 X |
| 5,029,090 | 7/1991 | Kuhn et al. | 180/197 X |
| 5,046,461 | 9/1991 | Kanehiro et al. | 180/197 X |

FOREIGN PATENT DOCUMENTS

| 0363570 | 4/1990 | European Pat. Off. |
| 3423116 | 1/1985 | Fed. Rep. of Germany. |
| 3516399 | 11/1986 | Fed. Rep. of Germany. |
| 3912014 | 10/1990 | Fed. Rep. of Germany. |
| 1207692 | 10/1970 | United Kingdom. |

OTHER PUBLICATIONS

Highway Research Record, No. 214, Dec. 1968, H. Domandl et al., "Measuring Tire Friction Under Slip With the Penn State Road Friction Tester", Highway Research Record.

*Primary Examiner*—Thomas G. Black
*Assistant Examiner*—Thomas S. Auchterlonie
*Attorney, Agent, or Firm*—Frishauf, Holtz, Goodman & Woodward

[57] ABSTRACT

An apparatus for effecting a method for estimating the friction coefficient of a road surface according to the present invention comprises front- and rear-wheel rotation sensors for detecting the running speed of a vehicle, a linear G sensor for detecting an actual transverse acceleration of the vehicle, a steering angle sensor for detecting the steering angle of front wheels, and a torque calculating unit supplied with the vehicle speed, actual transverse acceleration, and steering angle detected by means of these sensors. In the torque calculating unit, which takes account of an assumed value of the stability factor of the vehicle in addition to the vehicle speed, actual transverse acceleration, and steering angle, a target transverse acceleration required by a driver is calculated, for example, and whether or not the friction coefficient of the road surface is low is then estimated according to the relationship between the calculated target transverse acceleration and the actual transverse acceleration.

10 Claims, 30 Drawing Sheets

APPARATUS AND A METHOD FOR ESTIMATING THE FRICTION COEFFICIENT OF A ROAD SURFACE AND CONTROLLING A DRIVING CONDITION OF A VEHICLE IN ACCORDANCE WITH THE ESTIMATED FRICTION COEFFICIENT

BACKGROUND OF THE INVENTION

1. Field of the Invention

The present invention relates to an apparatus and a method for estimating whether or not the friction coefficient of a road surface is low or the friction coefficient itself of the road surface while a vehicle is running.

The present invention further relates to an apparatus and a method for controlling a driving condition of a vehicle in accordance with the estimated friction coefficient of the road surface on which the vehicle is running, so that a stable running of the vehicle can be obtained.

2. Description of the Related Art

Detection of the friction coefficient of a road surface is essential to stable and smooth drive of a vehicle. If the road on which the vehicle is running changes from a dry ordinary road into a snow-covered or frozen road, the friction coefficient of the road surface suddenly lowers. When the vehicle runs on such a low-friction road, that is, a so-called low-$\mu$ road, the driving wheels of the vehicle are very liable to slip, so that it is extremely difficult to control the vehicle. If the driving wheels undergo a slip, a driver is expected to reduce the depth of depression of the accelerator pedal, thereby controlling the engine output, in order to stop the slip. It is very hard for even a skilled driver, however, to control the engine output by only adjusting the depth of depression of the accelerator pedal.

When the vehicle turns or circles, on the other hand, a centrifugal force or transverse acceleration acts on the vehicle at right angles to the running direction thereof. If the running speed of the vehicle is too high, therefore, the transverse acceleration may exceed the gripping force of tires, possibly entailing a skid of the vehicle. Such a skid of the vehicle tends to be caused especially when a gateway of the turning road cannot be found or when the radius of curvature of the turning road gradually decreases. This is because the driver cannot properly control the engine output or vehicle speed with ease in such a situation.

A conventional vehicle whose turning characteristic is represented by the so-called understeering performance cannot stably pass a turning road unless the driver additionally turns the steering wheel as the transverse acceleration acting on the vehicle increases while the vehicle is turning or circling. If a specific value for the vehicle is exceeded by the transverse acceleration acting thereon, however, the vehicle suffers a skid despite the additional turn of the steering wheel, so that the actual turning track of the vehicle deviates a target turning track which is imaged by the driver. This tendency is particularly noticeable in front-engined vehicles of the fron-wheel drive type whose turning characteristic is represented by a positive understeering performance.

In consideration of these circumstances, there are proposed various output control devices which can compulsorily lower the engine output, without regard to the depth of depression of the accelerator pedal by the driver, if the driving wheels suffer a slip or if the transverse acceleration acting on the vehicle increases to the turning limit. To effectively enjoy the functions of the output control devices of this type, the timing for the start of operation of the devices must be properly controlled.

However, the timing for the start of operation of the output control devices, that is, the point of time when a slip of the driving wheels begins or when the turning limit is reached by the transverse acceleration of the vehicle, greatly varies depending on the friction coefficient of the road surface on which the vehicle is running, that is, on whether or not the running road is a low-$\mu$ road. For these output control devices, therefore, it is very important properly to detect the friction coefficient itself of the road surface or whether or not the running road is a low-$\mu$ road. Meanwhile, the friction coefficient of the road surface is conventionally detected or measured by various methods. However, none of these conventional methods are suited for the output control devices of this type.

As described above, the conventional output control devices, which are used for the turning control of the vehicle, are expected properly to detect the friction coefficient of the road surface or determine whether the running road is a low-$\mu$ road, even while the vehicle is turning. There are no conventional methods, however, which fulfill these requirements.

SUMMARY OF THE INVENTION

A first object of the present invention is to provide an apparatus capable of discriminating a low-$\mu$ road, that is, of estimating the friction coefficient of a road surface, while vehicle is running, and even while it is turning. A second object of the invention is to provide a method for estimating the friction coefficient of the road surface while the vehicle is turning.

The above first object is achieved by an apparatus according to the present invention, which comprises: means for detecting the running speed of a vehicle; means for obtaining an actual transverse acceleration acting on the vehicle at right angles to the running direction thereof; means for detecting the steering angle of steerable wheels of the vehicle; estimating means for estimating the friction coefficient of a road surface or a road surface condition indicative of the friction coefficient by arithmetically processing the stability factor of the vehicle in addition to the vehicle speed, actual transverse acceleration, and steering angle obtained with use of the individual means; and means for producing a predetermined output in accordance with the result obtained with use of the estimating means.

The above second object is achieved by a method according to the present invention, which comprises: a process for obtaining the running speed of a vehicle, the steering angle of steerable wheels of the vehicle, and an actual transverse acceleration acting on the vehicle at right angles to the running direction thereof; an estimating process for estimating the friction coefficient of a road surface or a road surface condition indicative of the friction coefficient by arithmetically processing the stability factor of the vehicle in addition to the vehicle speed, actual transverse acceleration, and steering angle obtained in the aforesaid process; and a process for producing a predetermined output in accordance with the result obtained in the estimating process.

In estimating the friction coefficient of the road surface or the road surface condition indicative of the friction coefficient, according to the apparatus and the method described above, the stability factor of the vehicle, besides the vehicle speed, actual transverse acceleration, and steering angle, is taken into consideration, so that these informations are necessary and enough for a grasp of the turning conditions of the vehicle. Thus, the friction coefficient of the road surface and the road surface condition indicative of the friction coefficient, obtained by arithmetically processing the vehicle speed, actual transverse acceleration, steering angle, and stability factor, exhibit suitable estimation results for the turning control of the vehicle.

Preferably, according to the apparatus and the method described above, the upper limit valve of the stability factor of the vehicle on a road surface having a low friction coefficient is prepared as an assumed value. If this assumed value is prepared, the target transverse acceleration of the vehicle required by a driver is first calculated on the basis of assumed values of the vehicle speed, steering angle, and stability factor in the estimating process by means of the estimating means. Since this target transverse acceleration is calculated on the basis of the assumed value of the stability factor, it represents a transverse acceleration which is theoretically excessive when the vehicle turns on a road surface having a low friction coefficient. In the estimating process, therefore, the friction coefficient of the road surface can be discriminated by comparing the calculated target transverse acceleration and the actual transverse acceleration by using the estimating means. More specifically, if the target transverse acceleration is lower than the actual transverse acceleration, the friction coefficient of the road surface can be determined to be high. If the former is greater than the latter, on the other hand, it can be concluded that the friction coefficient of the road surface is low, that is, the running road is a low-$\mu$ road.

Meanwhile, in the apparatus and the method according to the present invention, a limit value of the stability factor is preferably preset for stable turning of the vehicle. If this limit value of the stability factor is prepared, the stability factor itself can be calculated on the basis of the vehicle speed, actual transverse acceleration, and steering angle so that the calculated stability factor and the limit value can be compared in the estimating process by means of the estimating means. If the calculated stability factor is greater than the limit value, it can be concluded in the estimating process that the control of the vehicle is unstable, that is, the limit of vehicle steering capacity is reached. Since the vehicle cannot be stably turned when the limit of vehicle steering is thus reached, an alarm is preferably given to the driver.

By only comparing the calculated stability factor and the limit value in the aforesaid manner, however, the driver cannot determine whether the limit of vehicle steering capacity is reached on a so-called high-$\mu$ road having a high friction coefficient or on a low-$\mu$ road. In the apparatus and the method of the present invention, therefore, a value intermediate between a maximum transverse acceleration of the vehicle obtainable on a high-$\mu$ road and a maximum transverse acceleration obtainable on a low-$\mu$ road is preferably preset as a discrimination value. In the estimation process, in this case, the actual transverse acceleration and the discrimination value are further compared by means of the estimating means when the limit value is exceeded by the calculated stability factor. If the value of the actual transverse acceleration is smaller than the discrimination value, it can be concluded that the limit of vehicle steering capacity on a low-$\mu$ road is reached, and at the same time, that the running road is a low-$\mu$ road.

If the comparison indicates that the calculated stability factor and the limit value are equal, the actual transverse acceleration of the vehicle is substantially equal to the friction coefficient of the road surface when the order is disregarded. Thus, according to the estimating means and the estimating process of the invention, the friction coefficient of the road surface can be estimated from the value of the actual transverse acceleration of the vehicle at the point of time when the calculated stability factor becomes equal to the limit value.

A third object of the present invention is to provide an apparatus and method for controlling a driving condition of a vehicle on the basis of the estimated friction coefficient of an actual road surface on which the vehicle is running, so that a stable running of the vehicle can be obtained.

The above and other objects, features, and advantages of the invention will be more apparent from the ensuing detailed description of illustrative embodiments thereof taken in connection with the accompanying drawings. It is to be understood that the drawings are for purpose of illustration only, and are not intended as a definition of the limits of the invention.

DETAILED DESCRIPTION OF THE PREFERRED EMBODIMENTS

Figure 1:
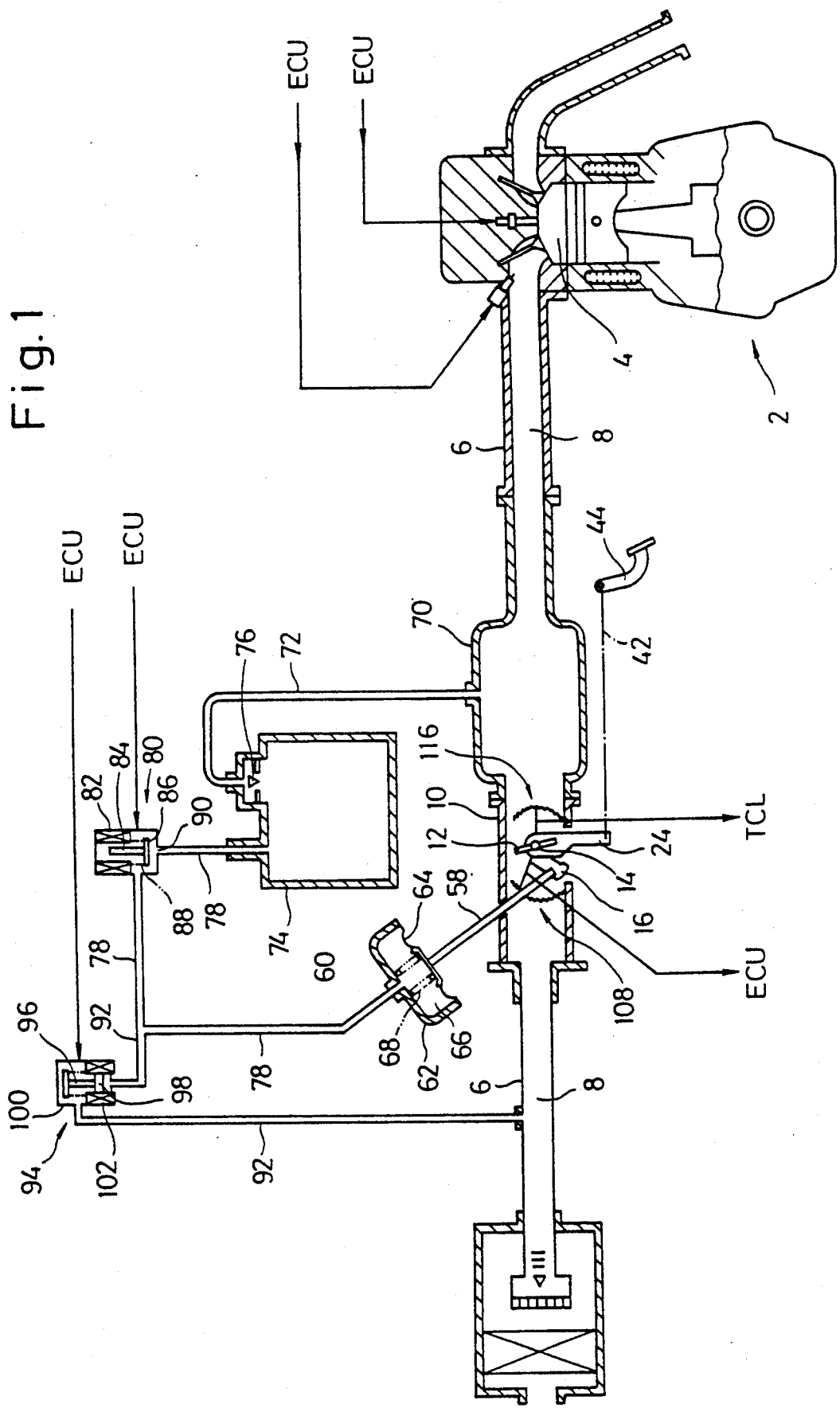
FIG. 1 is a schematic view showing a part of an output control device of a vehicle engine.
Figure 2:
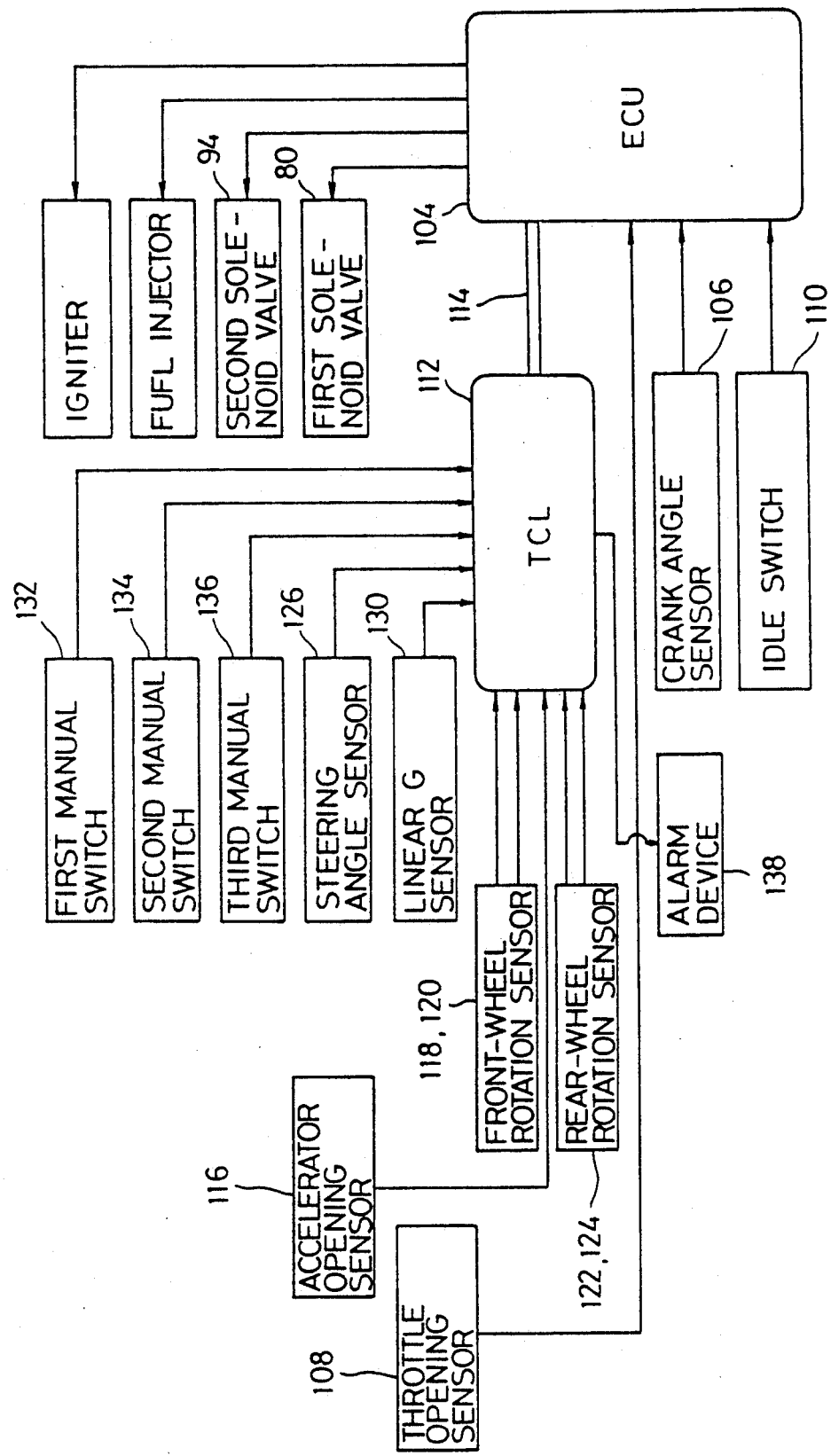
FIG. 2 is a schematic view showing a control system of the device of FIG. 1.

Referring to FIGS. 1 and 2, there are shown part of an internal combustion engine 2 and a control system for the engine 2, respectively. The engine 2 has a combustion chamber 4. A suction pipe 6 extends from the engine 2 so as to define a suction passage 8 which is connected to the chamber 4. A cylindrical throttle body 10 is provided in the middle of the suction pipe 6. The interior of the throttle body 10 defines part of the suction passage 8.

Figure 3:
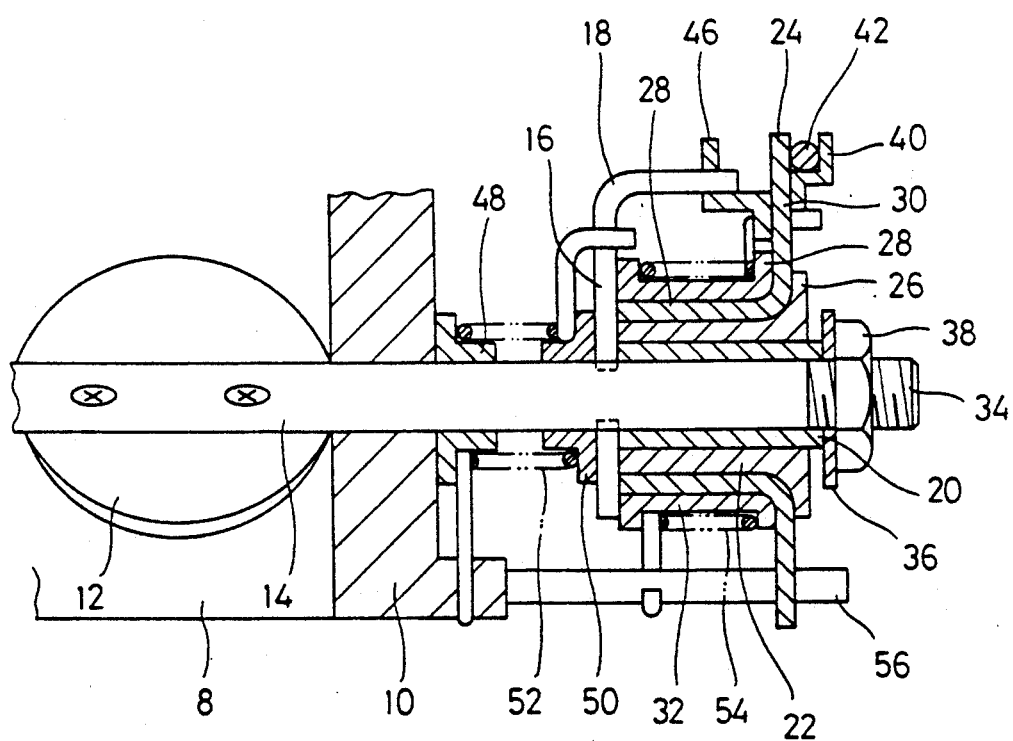
FIG. 3 is a sectional view showing a drive mechanism for a throttle valve of the engine of FIG. 1.

As shown in detail in FIG. 3, a throttle valve 12 is disposed in the throttle body 10. The valve 12 adjusts the intake of air introduced into the combustion chamber 4 in accordance with its opening, that is, throttle opening. The throttle valve 12 has a valve spindle 14, both ends of which are rotatably supported on the throttle body 10. One end of the spindle 14 projects outside the throttle body 10. A throttle lever 16 is fixedly mounted on the projecting portion of the valve spindle 14. Thus, the throttle lever 16 rotates integrally with the valve spindle 14. As seen from FIG. 3, the throttle lever 16 extends in the radial direction of the throttle spindle 14, and its distal end portion constitutes a stopper 18 which is bent toward the distal end of the spindle 14. Further, a bush 20 is mounted on the outer peripheral surface of the valve spindle 14 so as to be situated nearer to the distal end of the spindle 14 than the proximal end of the throttle lever 16 is. A spacer 22 and an accelerator lever 24 are successively mounted on the outer peripheral surface of the bush 20. A flange 26 is formed integrally on that end portion of the spacer 22 which is situated on the distal end side of the valve spindle 14. The flange 26 projects outward in the radial direction of the spacer 22.

An accelerator lever 24 is composed of a pipe portion 28, a lever portion 30 formed integrally on the pipe portion 28, and a collar portion 32 attached to the outer peripheral surface of the pipe portion 28. The pipe portion 28 of the accelerator lever 24 is rotatably mounted on the outer peripheral surface of the spacer 22. The portion 30 of the accelerator lever 24 extends radially outward beyond the flange 26, from the flange-side end portion of the spacer 22. Thus, the pipe portion 28 of the accelerator lever 24 is located between the throttle lever 16 and the flange 26 of the spacer 22. A screw portion 34 is formed at the distal end portion of the valve spindle 14, and a nut 38 is mounted on the screw portion 34 by means of a washer 36. The washer 36, which has a greater diameter than the bush 20, is pressed against the bush 20 by means of the nut 38. In the state shown in FIG. 3, the bush 20 projects slightly from the flange 26 of the spacer 22, so that a predetermined gap is defined between the flange 26 and the washer 36. Thus, the spacer 22 or the accelerator lever 24 is prevented from slipping off the valve spindle 14 by the washer 36 and the nut 38.

A wire guide 40 is mounted on the distal end portion of the lever portion 30 of the accelerator lever 24. The wire guide 40 is connected with one end of an accelerator wire 42. The wire 42 extends toward an accelerator pedal 44, as shown in FIG. 1, after being guided along the wire guide 40. The other end of the wire 42 is connected to the pedal 44. Thus, when the accelerator pedal 44 is pushed down, the accelerator wire 42 is pulled, so that the accelerator lever 24 is rocked around the valve spindle 14 depending on the depression of the pedal 44.

The collar portion 32 of the accelerator lever 24 is sandwiched between the lever portion 30 of the lever 24 and the throttle lever 16, and a flange is formed on each end of the collar portion 32. A pawl 46 extends outward in the radial direction the collar portion 32 from that flange which is situated on the side of the accelerator lever 24. The pawl 46 can engage the stopper 18 of the throttle lever 16 as the accelerator lever 24 and the lever 16 rock relatively to each other. More specifically, the engagement between the pawl 46 and the stopper 18 is achieved when the throttle lever 16 is rocked in the direction to open the throttle valve 12 or when the accelerator lever 24 is rocked in the direction to close the valve 12.

A pair of spring seats 48 and 50 are mounted on the projecting portion of the valve spindle 14 so as to be situated between the throttle body 10 and the throttle lever 16. A torsion coil spring 52 is disposed between these spring seats so as to surround the projecting portion of the spindle 14. One end of the spring 52 is anchored to the throttle body 10, while the other end is retained on the throttle body 10. In this case, the torsion coil spring 52 urges the throttle lever 16 to rock it in a direction such that the stopper 18 of the lever 16 abuts against the pawl 46 of the accelerator lever 24, that is, in the direction to open the throttle valve 12.

A torsion coil spring 54 is also mounted on the collar portion 32 of the accelerator lever 24 so as to surround the same. One end of the spring 54 is anchored to a stopper pin 56, while the other end is anchored to the accelerator lever 24. The stopper pin 56 extends parallel to the projecting portion of the valve spindle 14 from the throttle body 10. In this case, the torsion coil spring 54 urges the accelerator lever 24 in a direction such that the pawl 46 of the lever 24 abuts against the stopper 18 of the throttle lever 16, that is, in the direction to close the throttle valve 12. Thus, the urging force of the spring 54 serves as a resistance to the depression of the accelerator pedal 44, whereby a driver can enjoy a so-called detent feeling when he or she steps on the pedal.

As shown in FIG. 1, one end of a control rod 58 is rockably connected to the distal end of the throttle lever 16. The other end side of the rod 58 is connected to a pneumatic actuator 60. More specifically, the actuator 60 is provided with a flat cylindrical shell 62 open at one end. The open end of the shell 62 is closed by means of a diaphragm 64. Thus, one side of the diaphragm 64 is exposed to the outside, and the other end of the control rod 58 is rockably connected to the outer surface of the diaphragm 64. The shell 62 and the diaphragm 64 define a pressure chamber 66 in conjunction with each other. A compression coil spring 68 is housed in the pressure chamber 66. Like the aforesaid torsion coil spring 52 (see FIG. 3), the spring 68 urges the throttle lever 16 through the medium of the control rod 58 in order to rock the lever 16 in the direction to open the throttle valve 12. Thus, the throttle lever 16, that is, the throttle valve 12, is urged in the valve opening direction by means of the resultant force of the torsion and compression coil springs 52 and 68. The resultant force of the springs 52 and 68 is smaller than the force of the aforesaid torsion coil spring 54, so that the valve 12 is closed when the accelerator pedal 44 is not worked.

As shown in FIG. 1, that part of the suction pipe 6 which is situated on the lower-course side of the throttle body 10 is formed as a surge tank 70. The tank 70 is connected to a negative-pressure tank 74 by means of a connecting line 72. A check valve 76, which is disposed between the line 72 and the tank 74, allows air only to flow from the tank 74 toward the tank 70. Thus, the negative-pressure tank 74 is kept at a negative pressure equal to the lowest pressure in the surge tank 70.

The negative-pressure tank 74 and the pressure chamber 66 of the pneumatic actuator 60 are connected by means of a connecting line 78. A first solenoid valve 80 is disposed in the middle of the line 78. The valve 80 is a normally-closed valve which is closed when its solenoid 82 is not energized. More specifically, the first solenoid valve 80 includes a plunger 84 which, having an valve plug 86 at an end portion thereof, is driven by means of the solenoid 82. When the solenoid 82 is not energized, the plunger 84 is moved downward (FIG. 1) by the urging force of a valve spring 88, so that the plug 86 rests on a valve seat 90. In FIG. 1, the valve plug 86 is disengaged from the seat 90.

A branch line 92 extends from that part of the connecting line 78 which is situated between the first solenoid valve 80 and the pneumatic actuator 60. The line 92 is connected to that part of the suction pipe 6 which is situated on the upper-course side of the throttle valve 12. A second solenoid valve 94, which is a normally-open valve, is disposed in the middle of the branch line 92. More specifically, a plunger 96 of the valve 94 is urged by means of a valve spring 100 so that its valve plug 98 is disengaged from its corresponding valve seat when a solenoid 102 of the valve 94 is not energied.

The first and second solenoid valves 80 and 94 are individually connected to an electronic control unit (ECU) 104 for controlling the operating conditions of the engine 2. The ECU 104 performs on-off control of the solenoids 82 and 102 of the first and second solenoid valves 80 and 94 on the basis of duty control. If the respective duty factors of the solenoid valves 80 and 94 are 0%, for example, the first valve 80 is closed, while the second valve 94 is open. Accordingly, the pressure chamber 66 of the pneumatic actuator 60 communicates with that part of the suction pipe 6 which is situated on the upper-course side of the throttle valve 12, so that the pressure in the chamber 66 is substantially equal to the atmospheric pressure. When the accelerator pedal 44 is depressed in this situation, therefore, the opening of the throttle valve 12 changes corresponding to the depth of depression of the pedal 44. If the respective duty factors of the first and second solenoid valves 80 and 94 are 100%, however, the first valve 80 is open, while the second valve 94 is closed. In this case, therefore, the pressure chamber 66 of the pneumatic actuator 60 communicates with the negative-pressure tank 74, so that the pressure in the chamber 66 is a negative pressure substantially equal to the negative pressure in the tank 74. Since the negative pressure in the pressure chamber 66 deforms the diaphragm 64 so as to reduce the capacity of the chamber 66, the control rod 58 is pulled diagonally upward to the left as in FIG. 1. Accordingly, the throttle lever 16 is rocked in the direction to close the throttle valve 12 by means of the control rod 58. Thus, the valve 12 is closed without regard to the state of the accelerator pedal 44, so that the driving torque of the engine 2 is forced to be reduced. As is evident from the above description, the opening of the throttle valve 12 can be varied without regard to the depth of depression of the accelerator pedal 44 by properly controlling the duty factors of the first and second solenoid valves 80 and 94, whereby the driving torque of the engine 2 can be adjusted to any desired value.

As shown in FIG. 2, a crank angle sensor 106 is connected to the ECU 104. The sensor 106, which is attached to the engine 2, supplies the ECU 104 with a detection signal corresponding to the engine speed NE. Further, a throttle opening sensor 108 and an idle switch 110 are connected to the ECU 104. The sensor 108, which is attached to the throttle body 10, supplies the ECU 104 with a detection signal corresponding to the throttle opening. The switch 110 detects the fully-closed state of the throttle valve 12, and supplies the ECU 104 with its detection signal.

Furthermore, the ECU 104 is connected with a torque calculating unit (TCL) 112 for calculating a target driving torque TO of the engine 2, by means of a communication cable 114. An accelerator opening sensor 116 is connected to the TCL 112. The sensor 116, like the throttle opening sensor 108 and the idle switch 110, is attached to the throttle body 10. The sensor 116 detects the opening or rocking angle of the accelerator lever 24, and supplies the TCL 112 with its detection signal. The detection signal delivered from the accelerator opening sensor 116 corresponds to the depth of depression of the accelerator pedal 44.

The TCL 112 is also connected with rotation sensors 118 and 120 for front wheels FWL and FWR, rotation sensors 122 and 124 for rear wheels RWL and RWR, a steering angle sensor 126, and a linear G sensor 128. The rotation sensors 118 and 120 detect the respective rotating speeds of left and right front wheels FWL and FWR for use as driving wheels, and supply the TCL 112 with their detection signals. Likewise, the rotation sensors 122 and 124 detect the respective rotating speeds of left and right rear wheels RWL and RWR for use as driven wheels, and supply the TCL 112 with their detection signals. The steering angle sensor 126 detects the rotational angle of a steering shaft 128 of a steering wheel, with respect to the state of straight drive of the vehicle, and supplies the TCL 112 with its detection signal. In other words, the sensor 126 detects the rotational angle of the steering shaft 128 with respect to its neutral position $\delta M$. The TCL 112 calculates the steering angle of the front wheels FWL and FWR for use as steerable wheels in accordance with the detection signal from the steering angle sensor 126. More specifically, if the rotational angle of the steering shaft 128 and the steering gear ratio are $\delta H$ and $\rho H$, respectively, the TCL 112 calculates the steering angle $\delta$ of the front wheels FWL and FWR according to $\delta = \delta H/\rho H$. The linear G sensor 130 detects an actual transverse acceleration GY of the vehicle, and supplies the TCL 112 with its detection signal. The TCL 112 is also supplied with detection signals from first, second, and third manual switches 132, 134 and 136, which will be mentioned later. Further, the TCL 112 is connected with an alarm device 138, such as a lamp or buzzer, which is located in the vicinity of the driver's seat of the vehicle.

The TCL 112 is supplied with the operating information of the engine 2, such as the intake of air, besides the engine speed NE from the ECU 104 and the detection signal from the idle switch 110, through the communication cable 114. On the other hand, the ECU 104 is supplied with information on the target driving torque TO of the engine 2 obtained in the TCL 112, through the cable 114.

Figure 4:
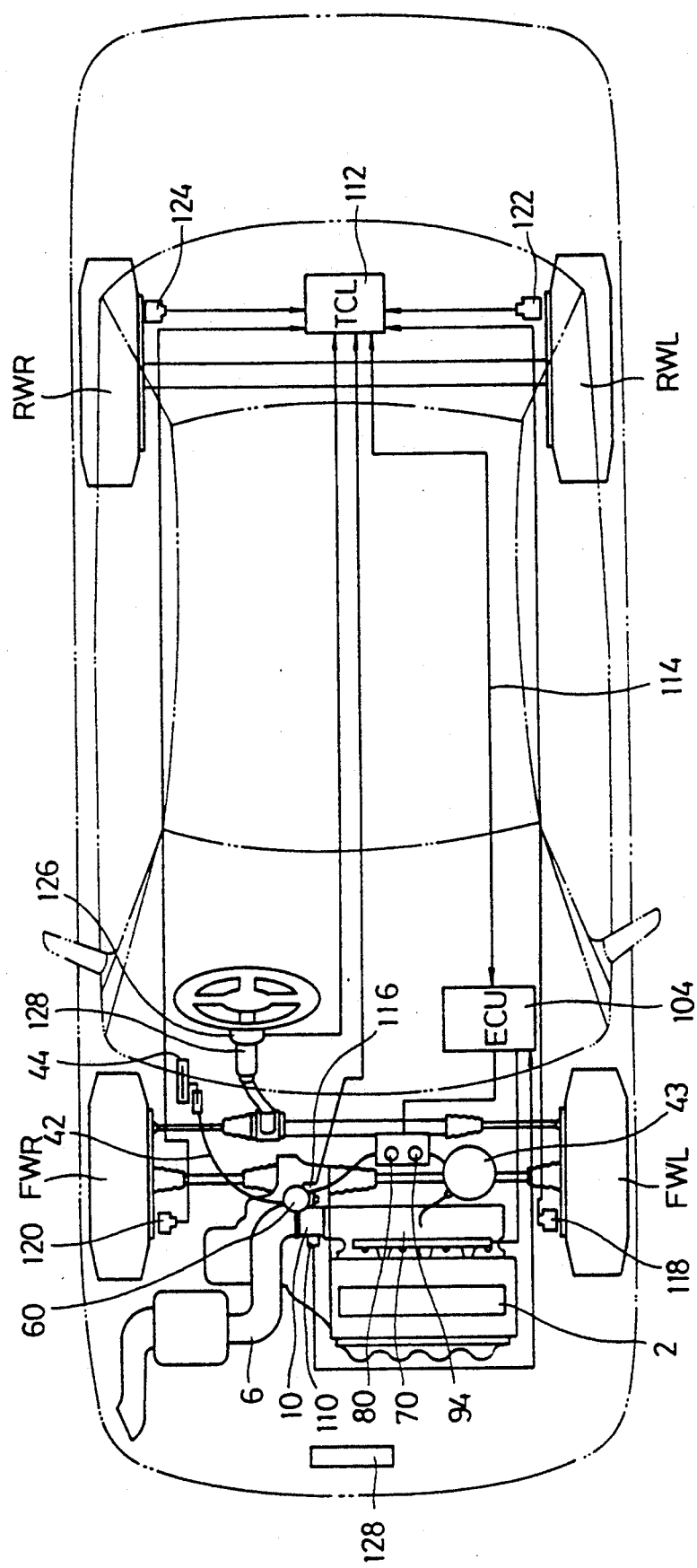
FIG. 4 is a diagram showing the arrangement of various parts constituting the output control device of FIGS. 1 and 2.

The arrangement of the TCL 112, various sensors and switches, and ECU 104 will be understood with reference to FIG. 4.

As mentioned before, the TCL 112 calculates the target driving torque TO of the engine 2, and supplies the ECU 104 with the result of the calculation. In order to calculate the target driving torque TO, the TCL 112 determines whether or not the road surface on which the vehicle runs is a low-$\mu$ road surface, at the same time.

Figure 5:
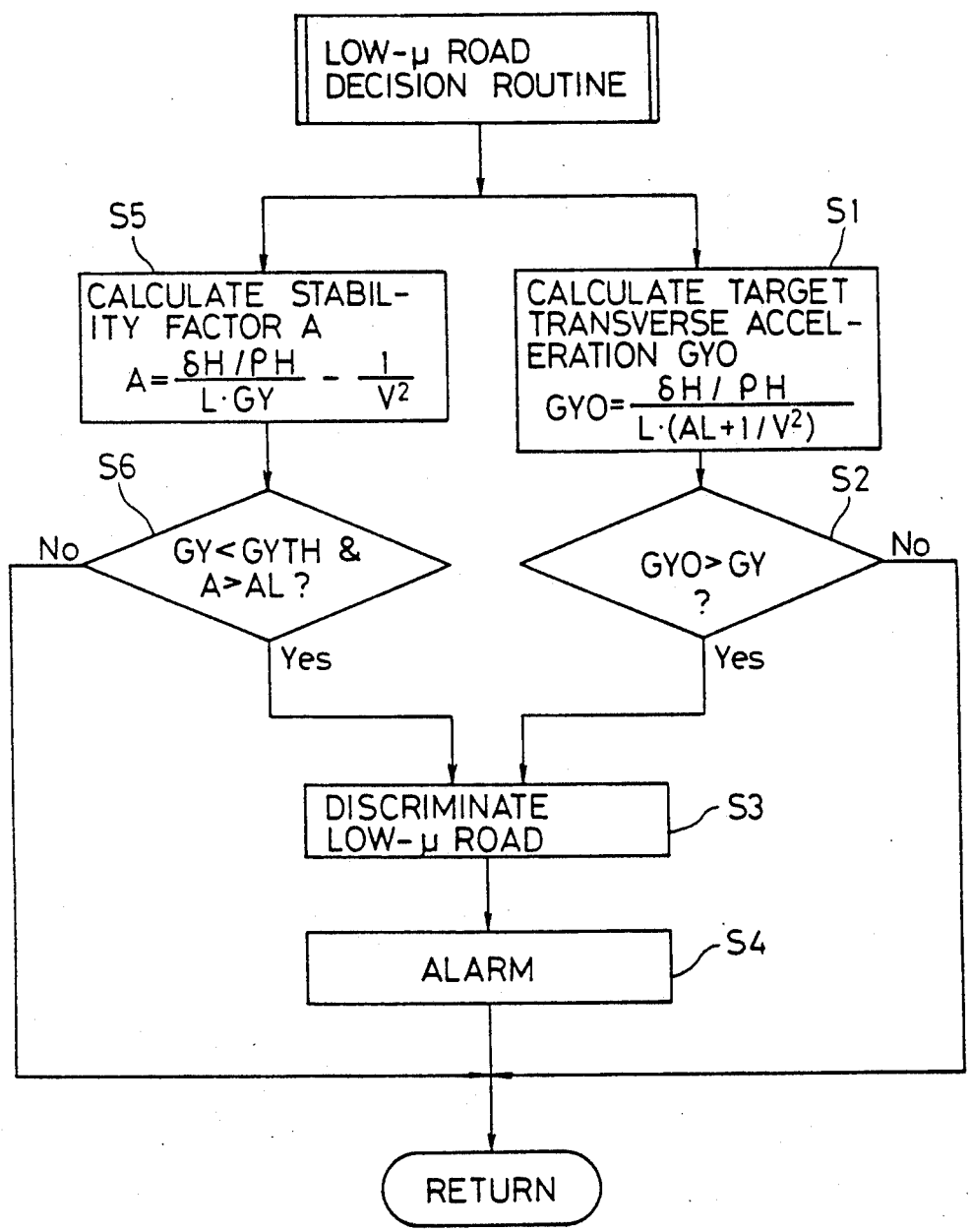
FIG. 5 is a flow chart showing a low-$\mu$ road decision routine executed by means of a torque calculation unit in the output control device of FIG. 2.

Referring to FIG. 5, there is shown a low-$\mu$ road decision routine which constitutes part of a calculation routine for the target driving torque TO executed in the TCL 112. Before describing the calculation routine for the target driving torque TO, the low-$\mu$ road decision routine will now be described with reference to FIG. 5.

Low-$\mu$ Road Decision Routine

Before executing the decision routine of FIG. 5, the TCL 112 first calculates a vehicle speed V according to the following equation on the basis of the detection signals from the rotation sensors 122 and 124 for the rear wheels RWL and RWR.

$V = (VRL + VRR)/2$, where VRL and VRR represent the peripheral speeds of the left and right rear wheels RWL and RWR, respectively. Thereafter, the TCL 112 executes Step S1 of the decision routine, whereupon a target transverse acceleration GYO, which can be guessed from the steering angle of the steering wheel, is calculated.

In general, the target transverse acceleration GYO is calculated as follows:

$GYO = (\delta H/\rho H)/\{L \cdot (A + 1/V^2)\}$.

According to the present embodiment, however, the target transverse acceleration GYO used for the decision of the low-$\mu$ road is calculated according to the following equation.

$GYO = (\delta H/\rho H)/\{L \cdot (AL + 1/V^2)\}$.

In these two equations, L is the wheel base of the vehicle, A is the stability factor, and AL is an assumed value of the stability factor of the vehicle on a low-$\mu$ road.

Figure 6:
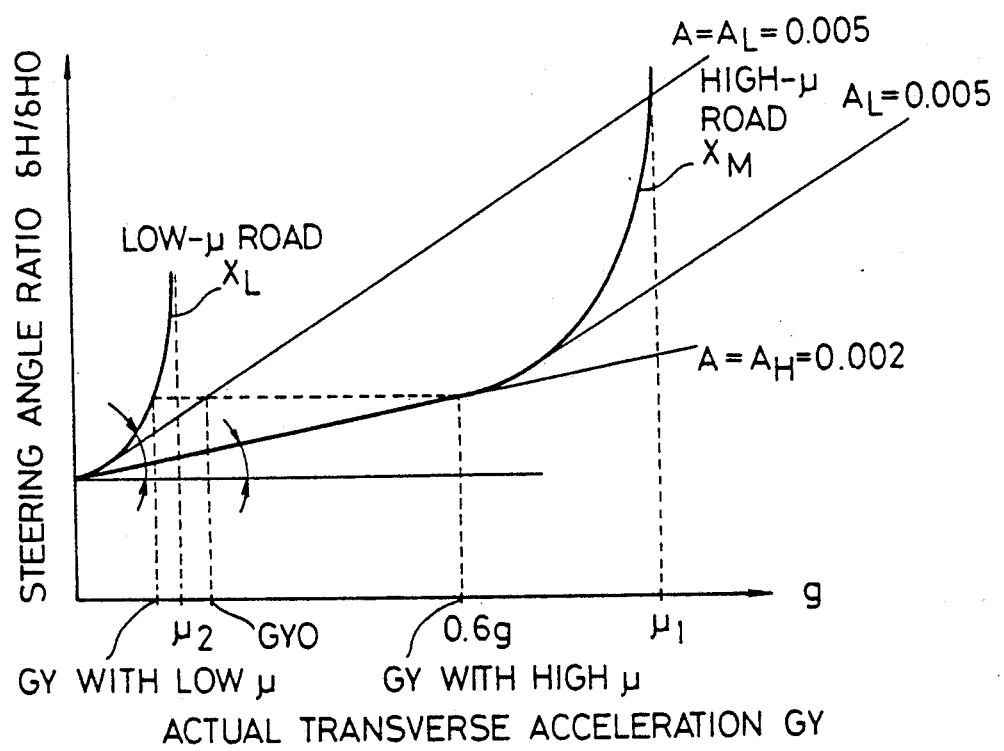
FIG. 6 is a graph showing the relationships between an actual transverse acceleration and the steering ratio of the vehicle used in the description of the decision routine of FIG. 5.

As is generally known, the stability factor A is a value which depends on the construction of the suspension system of the vehicle and the characteristics of the tires. Since the tire characteristics greatly vary depending on the road surface conditions, the stability factor A can be specifically given as an inclination of a tangent which touches the characteristic curve of FIG. 6 at any desired point. In FIG. 6, the axes of abscissa and ordinate represent the actual transverse acceleration GY and steering angle ratio $\delta H/\delta HO$, respectively. Symbol $\delta HO$ indicates the rotational angle of the steering shaft 128, with respect to its neutral position $\delta M$, obtained when the vehicle can enjoy a very-low-speed run such that the actual transverse acceleration GY is nearly zero. Thus, in a normal-speed running state, the steering angle ratio $\delta H/\delta HO$ indicates the ratio of $\delta H$ to $\delta HO$.

In FIG. 6, a characteristic curve XH represents a case in which the vehicle makes steady-state circular turning on a standard high-$\mu$ road, such as a dry paved road, on the assumption that the vehicle speed V is not very high. A characteristic curve XL represents a case in which the vehicle makes steady-state circular turning on a low-$\mu$ road, such as a rain-wet road or an icy-snow- or ice-covered road. The curves of FIG. 6 are obtained as a result of test runs of a front drive vehicle, as in the case of the present embodiment. If the friction coefficient of the high-$\mu$ road is $\mu 1$, the value of the actual transverse acceleration GY never exceeds the value of the friction coefficient $\mu 1$ when the order is disregarded, as seen from the characteristic curve XH. In the region where the value of the actual transverse acceleration GY is smaller than the value of the friction coefficient $\mu 1$, the characteristic curve XH is substantially linear on the assumption that the vehicle speed V is not very high. Accordingly, the stability factor A for this region takes a substantially constant value (e.g., $A = 0.002$). When the actual transverse acceleration GY exceeds the upper limit of this region, e.g., 0.6 g, however, the characteristic curve XH suddenly rises. Thus, even though the steering angle ratio $\delta H/\delta HO$ increases, the increasing rate of the actual transverse acceleration GY lowers. In this case, therefore, the stability factor A also increases drastically, so that the turning characteristic of the vehicle exhibits extreme understeering.

The characteristic curve XL for the low-$\mu$ road has the same characteristic as the characteristic curve XH. If the friction coefficient of the low-$\mu$ road is $\mu 2$ ($\mu 2 < \mu 1$), the value of the actual transverse acceleration GY cannot exceeds the value of the friction coefficient $\mu 2$. When the value of the actual transverse acceleration GY approaches the value of the friction coefficient $\mu 2$, the stability factor A suddenly increases.

If the value of the stability factor A is set at the aforesaid assumed value AL (e.g., AL=0.005) as a critical value obtained in the region where the characteristic curve XL is relatively linear, the target transverse acceleration GYO calculated according to the aforementioned equation exhibits a transverse acceleration which is allowed when the vehicle runs stably on the low-$\mu$ road at the then speed V. The graph of FIG. 6 shows the case of a vehicle whose steering characteristic is understeering. However, characteristic curves similar to the characteristic curves XH and XL of FIG. 6 can be also obtained for a vehicle whose steering characteristic is oversteering. Thus, the calculated target transverse acceleration GYO and the actual transverse acceleration GY are compared in Step S2. When the target transverse acceleration GYO is higher than the actual transverse acceleration GY, that is, when we have GYO>GY, it may be concluded that the road on which the vehicle is running is a low-$\mu$ road. The actual transverse acceleration GY can be obtained according to the detection signal from the linear G sensor 130. When the program proceeds from Step S2 to Step S3, therefore, the discrimination of the low-$\mu$ road is determined in Step S3. In Step S4, thereafter, an alarm is delivered from the aforementioned alarm device 138. This alarm informs the driver of the slipperiness of the road surface.

Steps S5 and S6 are executed simultaneously with the execution of Steps S1 and S2 in parallel relation. In Step S5, the stability factor A is calculated according to the following equation.

$$A=(\mu H/\rho H)/(GY\cdot L)-1/V^2.$$

This equation is obtained by rearranging the aforesaid calculation formula for the target transverse acceleration GYO with respect to the stability factor A. In Step S6, the calculated stability factor A and the assumed value AL are compared, and the actual transverse acceleration GY and a predetermined value GYTH are compared. If we have A>AL and GY<GYTH, the decision in Step S6 is YES, and it is concluded in Step S3 that the running road is a low-$\mu$ road. Thereafter, the program proceeds to Step S4, whereupon an alarm is delivered in like manner.

Figure 7:
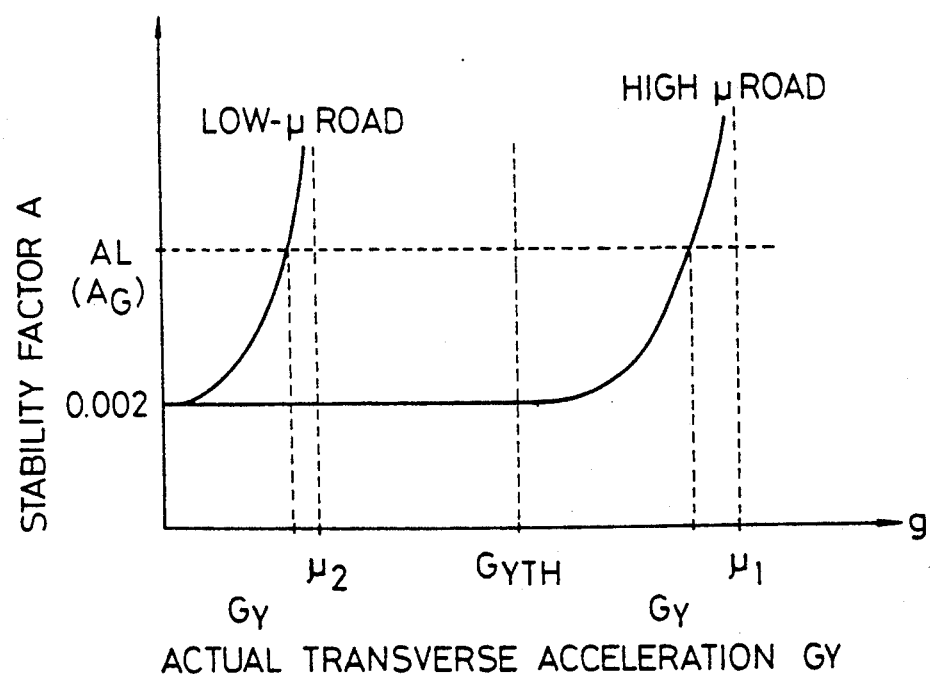
FIG. 7 is a graph similar to FIG. 6, showing the relationships between the actual transverse acceleration and the stability factor of the vehicle.

As seen from FIG. 7, the predetermined value GYTH is set at a value intermediate between the friction coefficient $\mu 1$ of the high-$\mu$ road and the friction coefficient $\mu 2$ of the low-$\mu$ road. In this case, the value GYTH is 0.5 g. In FIG. 7, the axis of abscissa represents the actual transverse acceleration GY, as in FIG. 6, and the axis of ordinate represents the inclination of a tangent which touches each of the characteristic curve XH and XL at any desired point, that is, the stability factor A. In FIG. 7, moreover, characteristic curves YH and YL represent the cases of the high- and low-$\mu$ roads, respectively. Thus, FIG. 7 more evidently reveals the relationships between the actual transverse acceleration GY and the stability factor A for the cases of the high- and low-$\mu$ roads. If the result of decision in Step S6 of FIG. 5 is YES, then the stability factor A is higher than the assumed value AL corresponding to the allowable transverse acceleration, that is, the friction coefficient of the running road is approximate to the friction coefficient $\mu 1$ of the low-$\mu$ road. Accordingly, the discrimination of the low-$\mu$ road can be executed also by determining whether or not A>AL holds. Also in the case of the high-$\mu$ road, there is a region where the relation A>AL holds. In Step S5, however, it is determined whether or not A>AL and GY<GYTH simultaneously hold, so that the discrimination of the low-$\mu$ road can be executed securely and accurately. In the low-$\mu$ road decision routine described above, it is concluded that the running road is a low-$\mu$ road when the result of decision in Step S2 or S5 is YES. Alternatively, however, the discrimination of the low-$\mu$ road may be determined in Step S3 only when both the results of decision in Steps S2 and S5 are YES. In this connection, the running road is presumed to be a high-$\mu$ road when Step S3 is not executed. In the low-$\mu$ road decision routine shown in FIG. 5, the processes of decision of Steps S2 and S5 are executed in the aforesaid manner so that it is determined whether or not the road on the which vehicle is running is a low-$\mu$ road.

Figure 8:
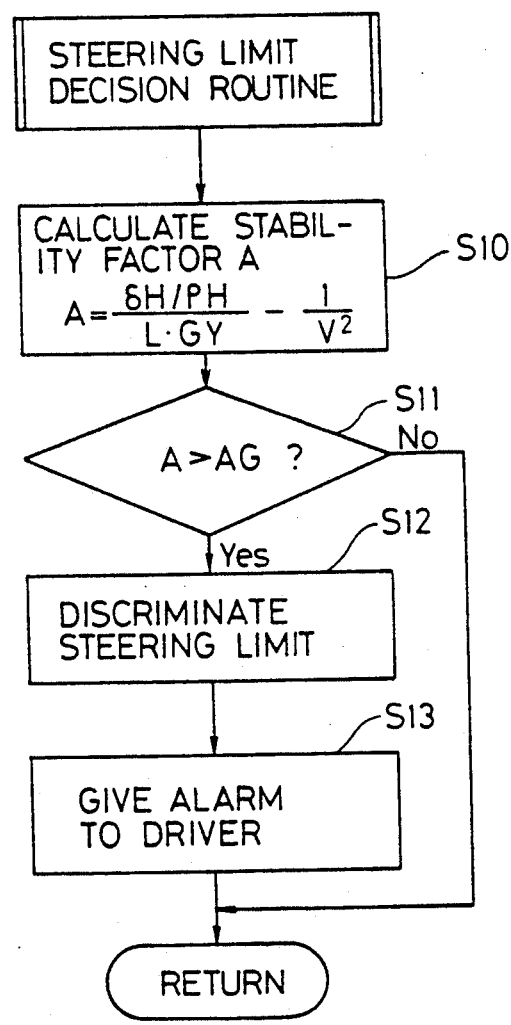
FIG. 8 is a flow chart showing a decision routine for the limit capacity of vehicle steering capacity of the vehicle executed by means of the torque calculation unit.

If a limit value AG for the stability factor A for stable turning of the vehicle is used in place of the assumed value AL so that it is determined in Step S6 whether or not A>AG holds, then the result of this decision also indicates whether or not the steering limit capacity is reached, as seen from FIGS. 6 and 7. In other words, if the stability factor A is greater than the assumed value AG, the actual transverse acceleration GY hardly increases, whether the running road is a low- or high-$\mu$ road, even though the steering wheel is further rotated, as shown in FIG. 6, so that this situation indicates the steering limit capacity. Thus, whether or not the steering limit capacity is reached can be determined by executing a decision routine shown in FIG. 8. The following is a brief description of the steering limit decision routine of FIG. 8.

Steering Limit Decision Routine

First, in Step S10, the stability factor A is calculated in the same manner as in Step S5 of FIG. 5, and it is determined in Step S11 whether or not the stability factor A is greater than the limit value AG (=AL). If the result of decision in Step S11 is YES, it is concluded in Step S12 that the steering limit capacity is reached. In Step S13, thereafter, an alarm is delivered from the aforementioned alarm device 138. This alarm informs the driver that the stable turning of the vehicle cannot be maintained if the driver further steers.

The TCL 112 repeatedly executes the aforementioned low-$\mu$ road decision routine or the steering limit decision routine with a predetermined sampling period. While the vehicle is running, therefore, the decision as to whether or not the running road is a low-$\mu$ road or whether or not the steering limit capacity is reached is continually made. The actual transverse acceleration GY need not always be detected by means of the linear G sensor 130. For example, it may be calculated according to the following equation based on the difference between the respective peripheral speeds of the left and right rear wheels RWL and RWR, that is,

|VRL−VRR|, tread b of the vehicle, and vehicle speed V.

$$GY = (|VRL - VRR| \cdot V)/(3.6^2 \cdot b \cdot g).$$

The following is a description of the procedure of calculation of the target driving torque TO of the engine 2 made by means of the TCL 112 and output control of the engine 2 effected in accordance with the calculated target driving torque TO, utilizing the aforementioned low-$\mu$ road decision routine.

Figure 9:
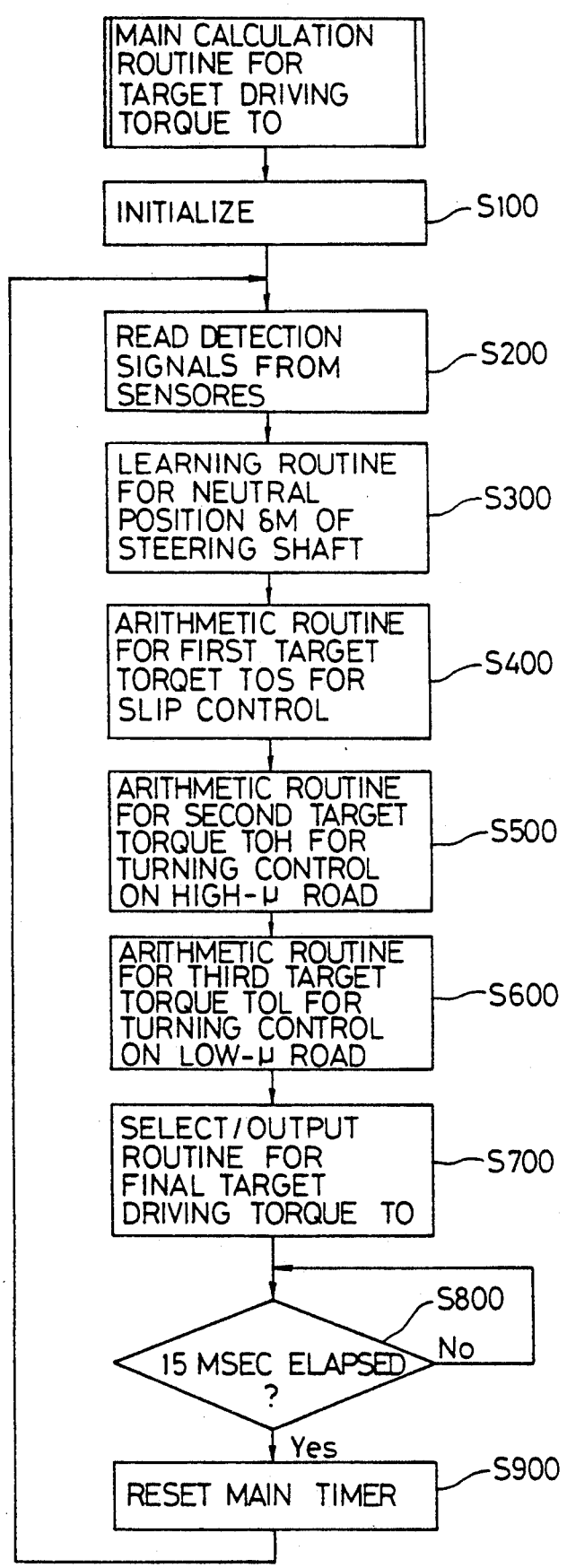
FIG. 9 is a flow chart showing a main routine for the calculation of a target driving torque of the engine executed by means of the torque calculation unit.

FIG. 9 shows a main calculation routine for the target driving torque TO, which will first be described in the following.

Main Calculation Routine

The main calculation routine is started when an ignition key (not shown) of the engine 2 is turned on, and initialization is executed in Step S100. In this initialization process, a main timer starts and various flags are reset. The main timer is a subtraction timer whose initial value is 15 msec as the sampling period for the main calculation routine.

In Step S200, the TCL 112 reads the detection signals from the various sensors. When the rotational angle $\delta H$ of the steering shaft 128 of the steering wheel is first detected from the steering angle sensor 126, it is set as the neutral position $\delta M$ of the shaft 128. The neutral position $\delta M$ is stored in a memory (not shown) in the TCL 112.

In Step S300, the neutral position $\delta M$ of the steering shaft 128 is corrected by learning. The neutral position $\delta M$ is first set at a reference position $\delta m(0)$ obtained in Step S100. When the vehicle fulfills requirements for stable straight drive, the neutral position $\delta M$ is corrected in accordance with learning control mentioned later. This learning correction is continued until the ignition key is turned off.

In Step S400, a first target torque TOS for slip control is calculated. It is used to regulate the driving torque of the engine 2 in accordance with the difference in rotation between the front and rear wheels FW and RW. In Step S500, a second target torque TOH is calculated. It is used to regulate the driving torque of the engine 2 as required when the vehicle turns on a high-$\mu$ road with a relatively high friction coefficient, such as a dry road. In Step S600, moreover, a third target driving torque TOL is calculated. It is used to regulate the driving torque of the engine 2 as required when the vehicle turns on a low-$\mu$ road with a relatively low friction coefficient, such as a frozen or wet road.

When the first to third target driving torques TOS, TOH and TOL are calculated, an optimum target driving torque TO is selected from the first to third target driving torques in Step S700, and is delivered to the ECU 104. In Step S800, it is determined whether or not the value in the main timer is 0, that is, whether or not 15 msec, the initial value of the main timer, has passed. If the decision in Step S800 is NO, the process of Step S800 is repeatedly executed. When the decision in Step S800 becomes YES, the program proceeds to Step S900, whereupon the value in the main timer is reset to the initial value. Thereafter, the processes of Steps S200 to S900 are repeatedly executed until the ignition key is turned off. Thus, when the final target driving torque TO is calculated in Step S700, in the main calculation routine described above, the delivery of the target driving torque TO is continued until the decision of Step S800 becomes YES. While the target driving torque TO is being delivered in this manner, the ECU 104 controls the respective duty factors of the first and second solenoid valves 80 and 94, in order to adjust the driving torque of the engine 2 to the target driving torque TO, so that the vehicle can smoothly run in stableness.

The neutral position $\delta M$ of the steering shaft 128 is corrected by learning in Step S300 for the following reason. For example, the neutral position $\delta M$ may change due to a deviation of the rotational angle $\delta H$ of the steering shaft 128 with relation to the steering angle $\delta$ of the front wheels FW, caused when the front wheels FW are subjected to toe-in adjustment at the time of vehicle maintenance, or caused by secular change attributable to abrasion of steering gears and the like. In executing the aforementioned decision routines of FIGS. 5 and 8, therefore, the stability factor A and the target transverse acceleration GYO can be accurately calculated if the rotational angle $\delta H$ of the steering shaft 128 is detected in consideration of the neutral position $\delta M$ corrected by learning.

Figure 10:
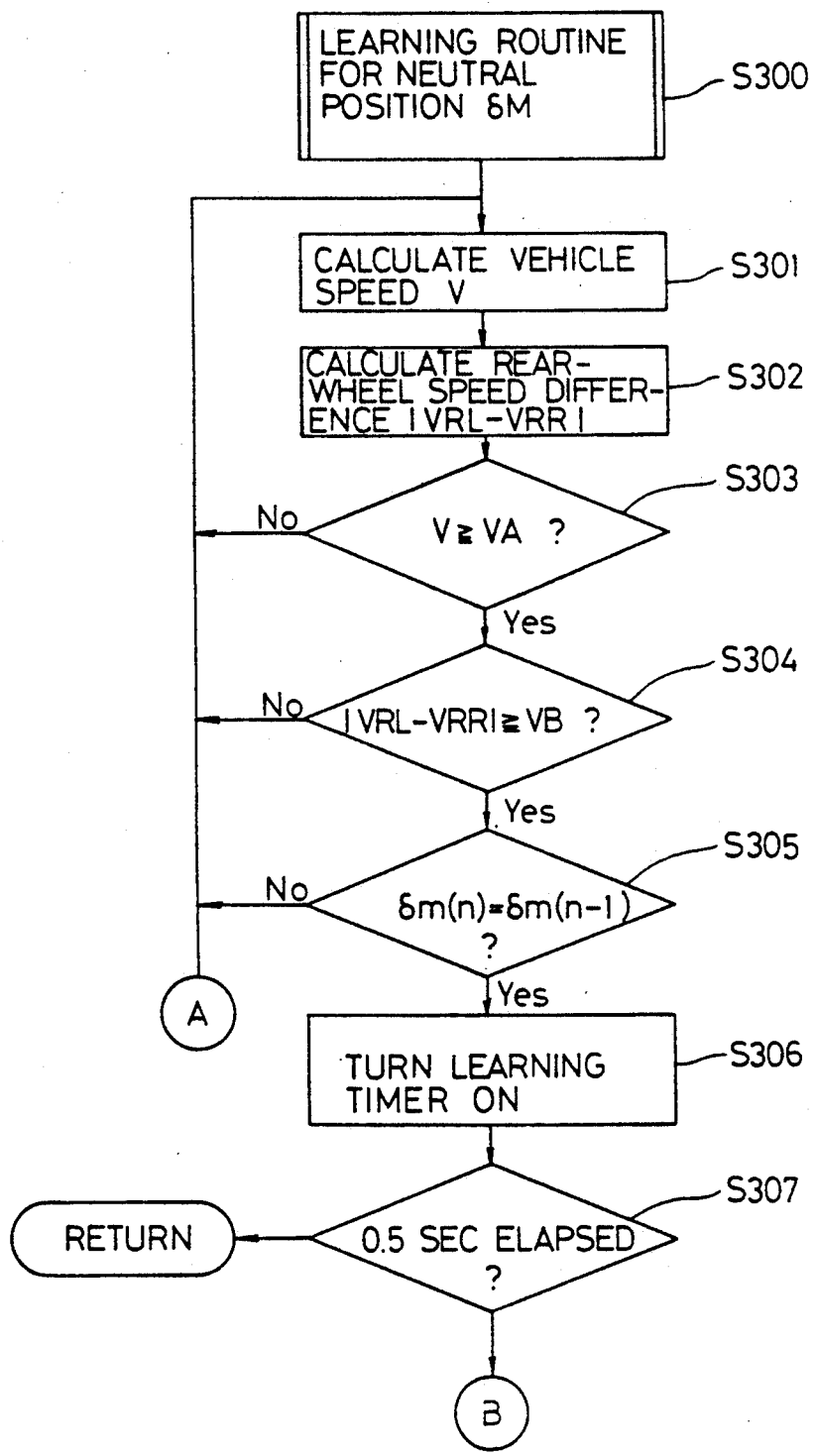
FIGS. 10 and 11 are flow charts showing the detail of a learning routine shown in FIG. 9.
Figure 11:
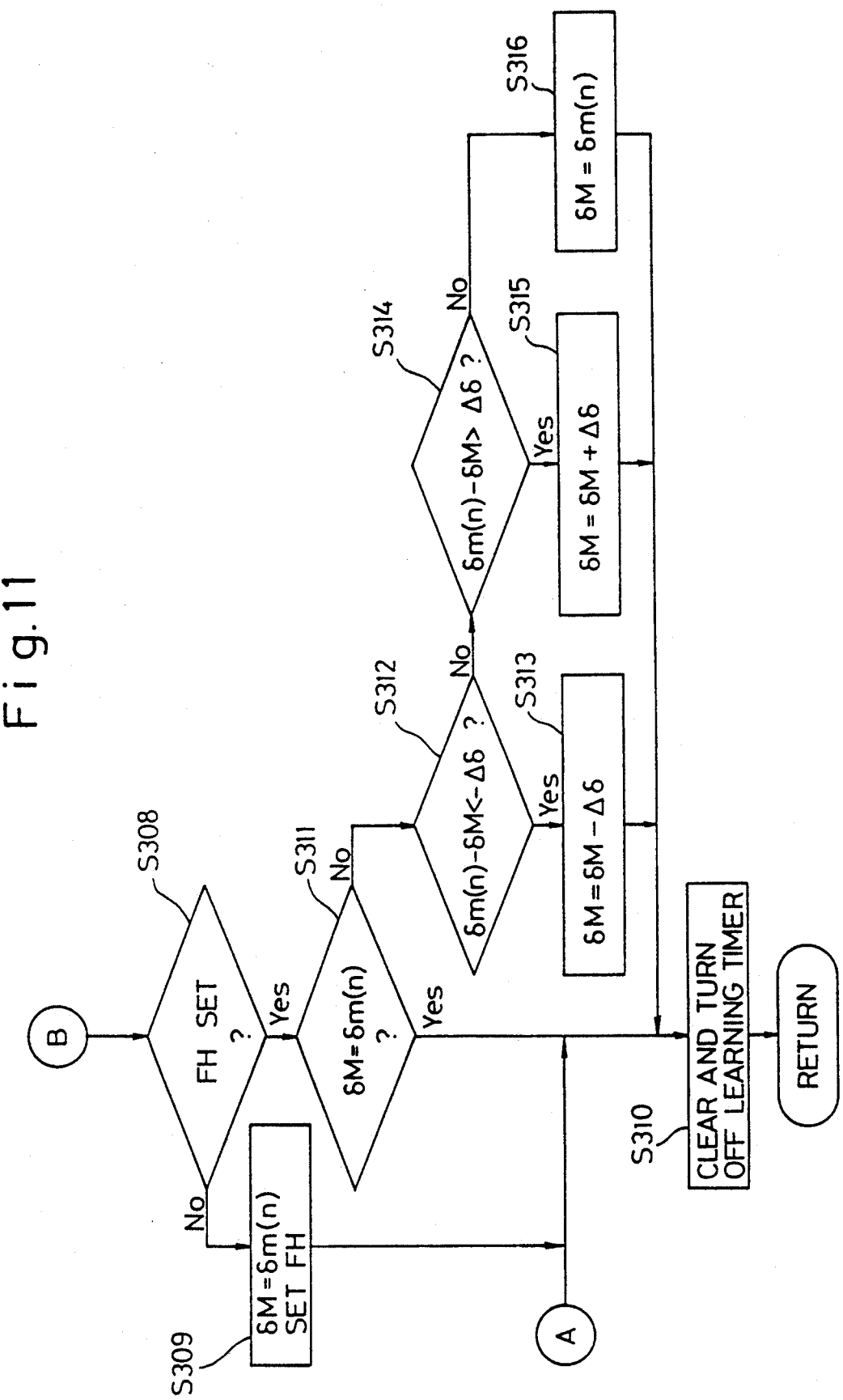

FIGS. 10 and 11 show the detail of Step S300, that is, a learning routine for correcting the neutral position $\delta M$ of the steering shaft 128. The following is a description of this learning routine.

Learning Routine

In this learning routine, the vehicle speed V is first calculated in Step S301. More specifically, the vehicle speed V is calculated as follows:

$$V = (VRL + VRR)/2 \qquad (1)$$

In Step S302, a deviation between the respective peripheral speeds of the rear wheels RWL and RWR (hereinafter referred to as rear-wheel speed difference), that is, |VRL−VRR|, is calculated. In Step S303, it is determined whether or not the vehicle speed V is higher than a preset threshold value VA. The decision in this step is necessary because the rear-wheel speed difference |VRL−VRR|, which is produced by the vehicle steering, cannot be detected unless the vehicle speed V reaches some high-speed zone. The threshold value VA, which is experimentally set in accordance with the running characteristics of the vehicle or the like, is adjusted to 20 km/h in this embodiment.

When the decision in Step S303 becomes YES as the vehicle speed V reaches the threshold value VA or a higher level, it is determined in Step S304 whether or not the rear-wheel speed difference |VRL−VRR| is smaller than a preset threshold value VB. The threshold value VB is set at 0.1 km/h, for example. If the result of decision in Step S304 is YES, it can be concluded that the vehicle is advancing straight. If the threshold value VB is set at 0 km/h, the rear-wheel speed difference is caused due to the difference in air pressure between the left and right rear wheels RWL and RWR even though the vehicle is advancing straight, so that the result of decision in Step S304 is inevitably NO. If the decision in Step S304 is YES, that is, if it is concluded that the vehicle is advancing straight, it is determined in Step S305 whether or not the rotational angle $\delta H$ or a reference position $\delta m(n)$ of the steering shaft 128 read this time in Step S200 of the main calculation routine is coincident with a reference position $\delta m(n-1)$ read in the preceding cycle. In making the decision in Step S305, the detection resolution of the steering angle sensor 126 is preferably set at, e.g., 5° or thereabout, in terms of the rotational angle of the steering shaft 128, lest the decision be influenced by vibratory motion of the steering wheel due to idle motion of the driver's hands or the like. If the decision in Step S305 is YES, a built-in timer for the learning routine in the TCL 112 is actuated in Step S306, and it is then determined in Step S307 whether or not 0.5 sec is attained by the value in the learning timer. In this case, the decision in Step S307 is NO immediately after the execution of Step S306, so that the program returns to the main calculation routine of FIG. 9.

However, if the decision in Step S307 becomes YES as the main calculation routine or the learning routine is repeatedly executed, that is, if a state such that the results of decision in Steps S303 to S305 are all YES continues for 0.5 sec, the program proceeds to Step S308 shown in FIG. 11. In Step S308, it is determined whether or not a learning flag FH is set. This learning flag FH is used to indicate whether or not the learning control has already been executed. Since the learning flag FH is left reset by the initialization in Step S100 of the main calculation routine of FIG. 9, the decision in Step S308 is NO at this point of time, so that the program proceeds to Step S309. In Step S309, the previously set neutral position $\delta M$ is replaced with the reference position $\delta m(n)$ of the steering shaft 128 for the present point of time so that a new neutral position is established, and the learning flag FH is set.

Thereafter, the program proceeds to Step S310, whereupon the value in the learning timer is cleared, and the operation of this timer is stopped. Then, the program returns to the main calculation routine of FIG. 9. After the neutral position $\delta M$ of the steering shaft 128 is set in the aforesaid manner, the rotational angle $\delta H$ of the steering shaft 128 is calculated on the basis of the neutral position $\delta M$.

The program proceeds again from the main calculation routine to the learning routine, in which the decision of Step S308 is made. Thereupon, the result of decision in Step S308 is YES, so that it is concluded that the learning control has already been executed, and the program then proceeds to Step S311. In Step S311, it is determined whether or not the reference position $\delta m(n)$ of the steering shaft 128 for the present point of time is coincident with the previously set neutral position $\delta M$, that is, whether or not the following equation holds.

$$\delta m(n) = \delta M.$$

If the decision in Step S311 is YES, Step S310 is executed, whereupon the program returns to the main calculation routine. If the decision in Step S311 is NO, however, due to some play of various parts of the steering system, the program proceeds to Step S312, whereupon the processes of Step S312 and the subsequent steps are executed. Even if the result of decision in Step S311 is NO, in this case, the present reference neutral position $\delta m(n)$ cannot be set as the neutral position $\delta M$ of the steering shaft 128. Thus, a value obtained by adding or subtracting a preset limit value $\Delta \delta$ to or from the neutral position $\delta M$ is set as a new neutral position only when the absolute value of the deviation between the reference neutral position $\delta m(n)$ and the neutral position $\delta M$ is considerably different from the limit value $\Delta \delta$. The new neutral position thus obtained by the learning correction replaces the neutral position $\delta M$ stored in the memory in the TCL 112. More specifically, in the learning correction of the neutral position $\delta M$, it is determined whether or not the following relation holds is first determined in Step S312.

$$\delta m(n) - \delta M < -\Delta \delta.$$

If the decision in Step S312 is YES, a new neutral position $\delta M$ is calculated according to the following equation in Step S313.

$$\delta M = \delta M - \Delta \delta.$$

When obtaining the new neutral position by correcting the previously set neutral position $\delta M$, the correction amount for each cycle is limited to $-\Delta \delta$, as seen from this equation, so that the value of the neutral position cannot greatly vary from the precorrection neutral position $\delta M$. Accordingly, if the detection signal from the steering angle sensor 126 suffers noises, thereby becoming abnormal signals, for example, the neutral position $\delta M$ of the steering shaft 128 for the reference can never drastically change. Thus, adverse effects of the noises on the calculation of the neutral position $\delta M$ can be reduced. If the decision in Step S312 is NO, on the other hand, it is determined in Step S314 whether or not the following relation holds.

$$\delta m(n) - \delta M > \Delta \delta.$$

If decision in Step S314 is YES, the previously set neutral position $\delta M$ is replaced with a new neutral position according to the following equation in Step S315.

$$\delta M = \delta M + \Delta \delta.$$

It is to be understood that the neutral position $\delta M$ of the steering shaft 128 can never drastically change, so that adverse effects of noises on the calculation of the neutral position $\delta M$ can be reduced also in this case.

If the decision in Step S314 is NO, that is, if the deviation between the reference position $\delta m(n)$ and the neutral position $\delta M$ is within $\pm \Delta \delta$, on the other hand, the previously set neutral position $\delta M$ is replaced with the present reference position $\delta m(n)$ in Step S316.

Any of Steps S313, S315 and S316 returns to the main calculation routine of FIG. 9 via Step S310.

Figure 12:
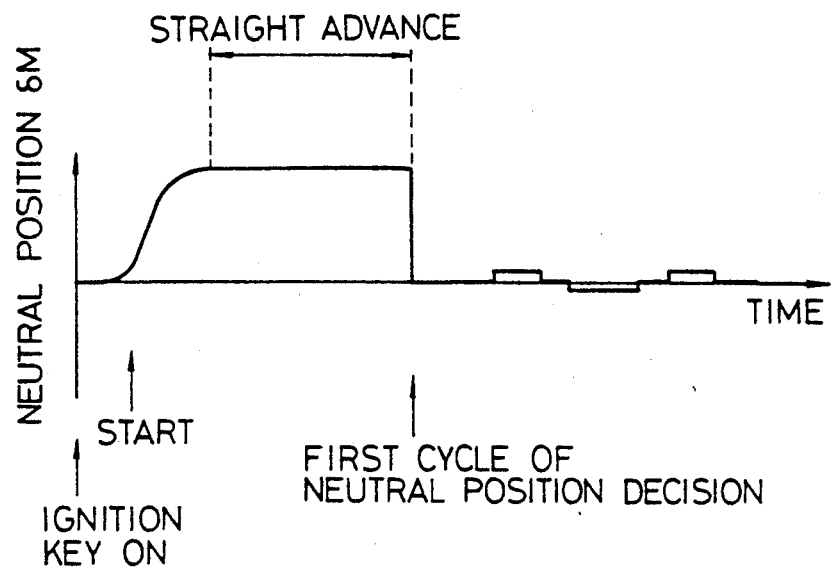
FIG. 12 is a graph showing an example of the result of learning obtained by the execution of the learning routine of FIG. 9.

FIG. 12 shows the way the neutral position $\delta M$ of the steering shaft 128 is corrected by learning, in starting the drive of the vehicle, having so far been at a stop with its front wheels FW kept turned, after turning on the ignition key. After the ignition key is turned on to start the drive, as seen from FIG. 12, Step S200 of FIG. 9 is executed for the first time, and the rotational angle $\delta H$ of the steering shaft 128 is read in response to the detection signal from the steering angle sensor 126. Thereupon, the first rotational angle $\delta H$ is set as the neutral position $\delta M$ of the steering shaft 128, as mentioned before, so that the neutral position $\delta M$ at the start of the drive of the vehicle is substantially deviated from the actual neutral position. When the learning routine of FIGS. 10 and 11 are executed so that the vehicle reaches a first straight drive state at a speed of 20 km/h or more, in these circumstances, the neutral position $\delta M$ is replaced with the reference position $\delta m(n)$ for the present point of time in Step S309. Thus, the neutral position $\delta M$ is greatly corrected for the first cycle only. If the learning routine S300 is repeatedly executed thereafter so that the vehicle fulfills the requirements for the straight drive, however, one of Steps S313, S315 and S316 is sure to be executed even though the result of decision in Step S311 is NO. In this case, therefore, the correction amount of the neutral position δM is restrained.

Figure 13:
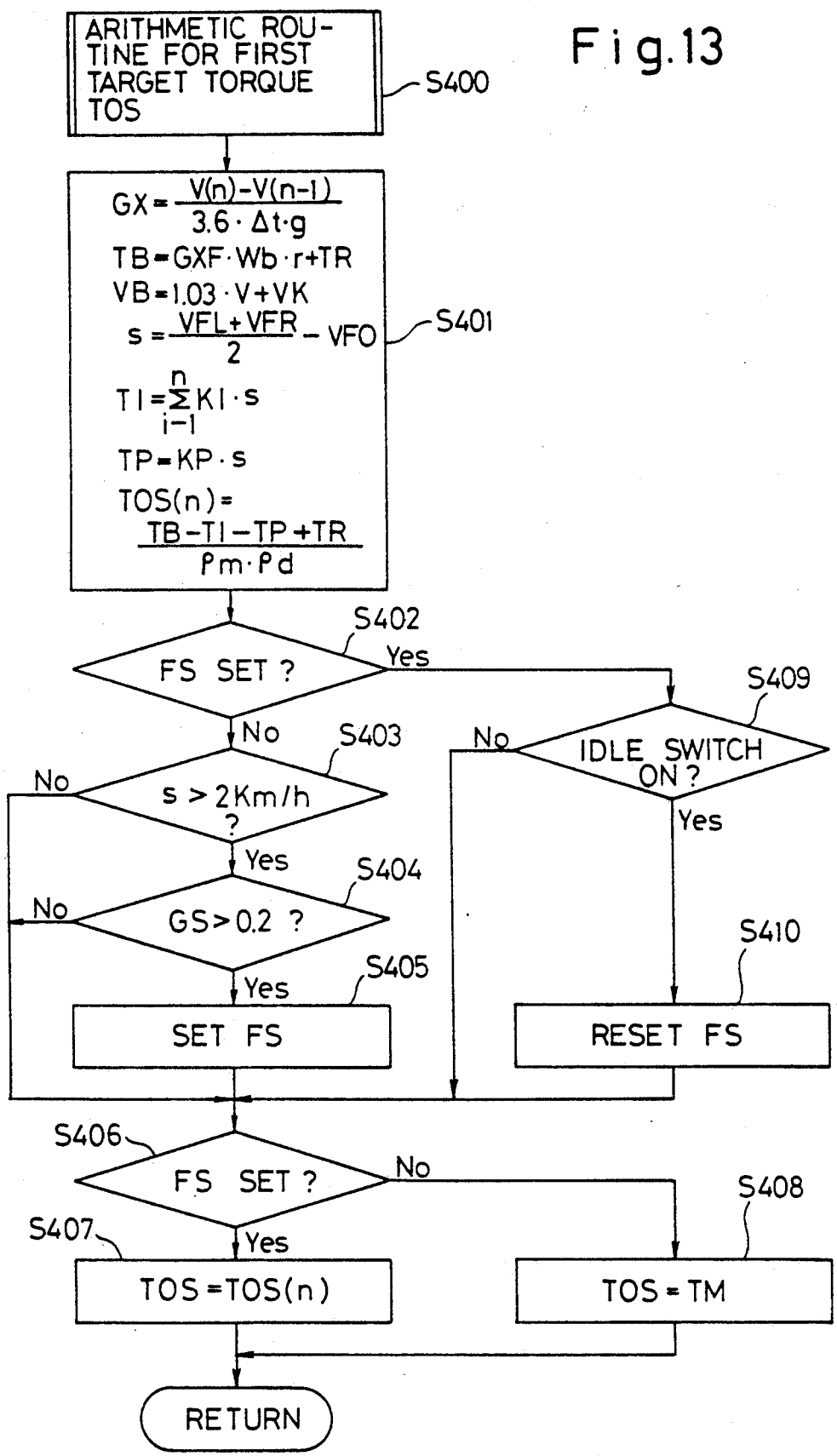
FIG. 13 is a flow chart showing the detail of an arithmetic routine for a first target torque shown in FIG. 9.

When the program returns to the main calculation routine of FIG. 9 after the learning routine of FIGS. 10 and 11 are executed, an arithmetic routine for the next first target torque is executed as aforesaid in the main calculation routine. FIG. 13 shows the detail of this arithmetic routine. The following is a description of the arithmetic routine for the first target torque TOS.

Arithmetic Routine for First Target Torque TOS

Figure 14:
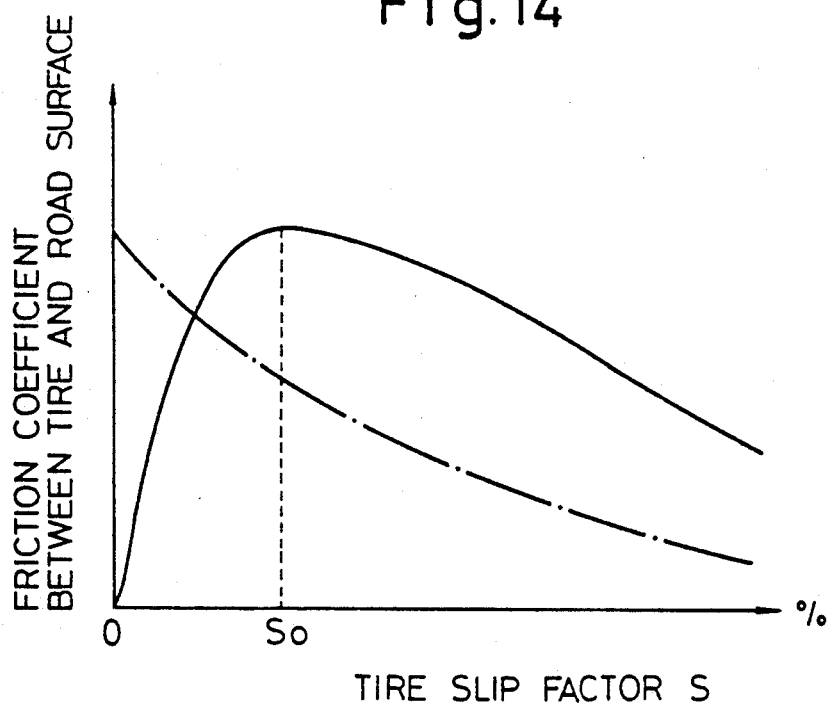
FIG. 14 is a graph showing the relationships between the slip factor of tires and friction coefficient used in the description of the arithmetic routine of FIG. 13.

First, in Step S401, a first target torque TOS(n) for the slip control at the present point of time is finally calculated. In order to advantageously perform the slip control by regulating the driving torque of the engine 2 in accordance with the first target torque TOS(n), the torque TOS(n) should be accurately calculated. To attain this, the first target torque TOS must be calculated in consideration of a slippage s of the tires of the driving wheels or front wheels FW. Referring now to FIG. 14, there is shown the friction coefficient between the tires of the front wheels FW and the road surface, compared with the slip factor S of the tires. As seen from FIG. 14, the friction coefficient has a maximum when the slip factor S is at a target slip factor So or in the vicinity thereof. If the driving torque of the engine 2 is regulated in accordance with the first target torque TOS(n), therefore, the slippage s of the front wheels FW should preferably be adjusted so that the slip factor S is at the target slip factor So or thereabout. If the slippage s of the front wheels is controlled in this manner, the acceleration performance of the vehicle cannot be lowered by the slip control. In FIG. 14, the dashed line represents the transverse drag of the tires.

The slip factor S of the front wheels can be calculated as follows:

$$S=\{(VFL+VFR)/2-V\}/V.$$

The following is a detailed description of the procedure of calculation of the first target torque TOS(n) made in Step S401. After the deviation between a vehicle speed V(n) calculated this time and a vehicle speed V(n−1) calculated in the preceding cycle, according to equation (1), is first calculated, a longitudinal acceleration GX with respect to the longitudinal direction of the vehicle is calculated. More specifically, the longitudinal acceleration GX is calculated as follows:

$$GX=(V(n)-V(n-1))/(3.6 \cdot \Delta t \cdot g),$$

where Δt indicates 15 msec or the sampling period of the aforementioned main timer, and g is acceleration of gravity.

Figure 15:
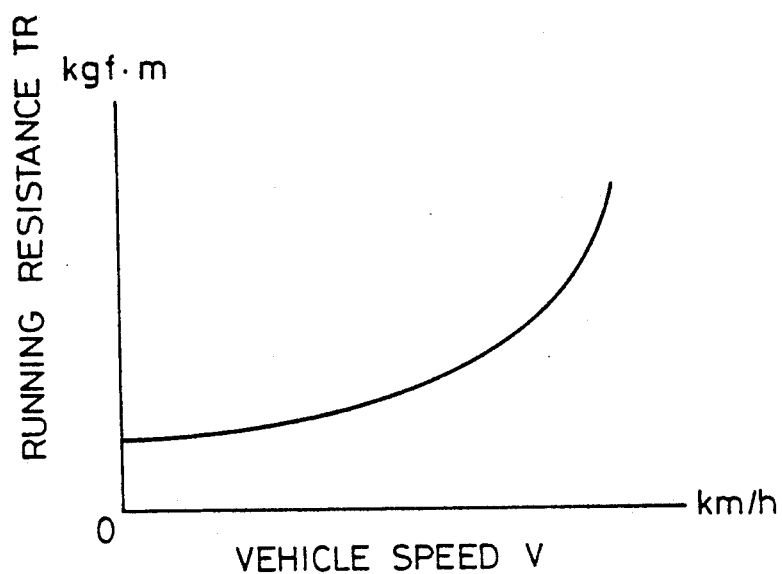
FIG. 15 is a graph showing the relationship between the vehicle speed and running resistance.

A driving torque TB of the engine 2 can be calculated as follows:

$$TB=GXF \cdot Wb \cdot r + TR, \qquad (2)$$

where GXF indicates a longitudinal acceleration obtained by processing the longitudinal acceleration GX by means of a low-pass filter. Since the filtered longitudinal acceleration GXF is a low-frequency component of the longitudinal acceleration GX, its change is subject to a delay behind the change of the longitudinal acceleration GX. In equation (2), moreover, Wb, r, and TR indicate the tare of the vehicle, effective radius of the front wheels FW, and running resistance, respectively. In this embodiment, the running resistance TR, which can be calculated as a function of the vehicle speed V, is obtained from the map of FIG. 15.

Figure 16:
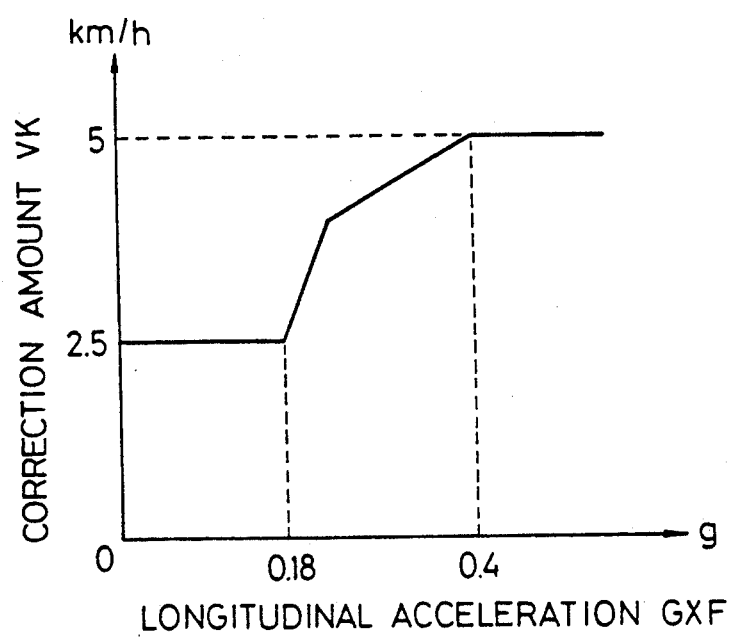
FIG. 16 is a graph showing the relationship between a longitudinal acceleration acting in the longitudinal direction of the vehicle and the correction amount of the vehicle speed.

The longitudinal acceleration GX can be regarded as equivalent to the friction coefficient between the tires of the front wheels FW and the road surface. As is evident from the foregoing equation, the driving torque TB of the engine can be made accurate and stable if it is calculated by using the longitudinal acceleration GXF in place of the longitudinal acceleration GX. Even while the vehicle is accelerating, the driving wheels normally have the slip factor S of 3% or thereabout. Meanwhile, the value of the friction coefficient with respect to the same target slip factor SO naturally varies depending on the conditions of the running road. Usually, the friction coefficient for a rough road, such as a gravel road, is higher than that for a low-μ road. Thus, a target peripheral speed VFO of the front wheels FW can be calculated according to the following equation in consideration of the slip factor S and the road surface conditions.

$$VFO=1.03 \cdot V + VK, \qquad (3)$$

where VK is the correction amount of the target peripheral speed VFO previously set corresponding to the longitudinal acceleration GXF. This correction amount VK increases by stages as the value of the longitudinal acceleration GXF increases. In this embodiment, the correction amount VK is read, in accordance with the longitudinal acceleration GXF, from the map of FIG. 16 which is created on the basis of the results of test runs of the vehicle and the like.

The slippage s of the front wheels FW can be expressed as the difference between the vehicle speed calculated from the respective peripheral speeds of the front wheels FW referring to equation (1) and the target peripheral speed VFO. Thus, the slippage s can be calculated as follows:

$$s=(VFL+VFR)/2-VFO. \qquad (4)$$

On the basis of the slippage s thus calculated, a correction torque TI (TI≤0) for improving the stability of the slip control based on the first target torque TOS(n) is calculated as follows:

$$TI=\Sigma KI \cdot s(i). \qquad (5)$$

As seen from this equation, the correction torque TI can be obtained by integrating or adding up values that are obtained by multiplying the slippage s by an integral coefficient KI for the individual sampling periods of the main timer.

Likewise, a correction torque TP for relieving the delay of the slip control is calculated as follows:

$$TP=KP \cdot s. \qquad (6)$$

As seen from this equation, the correction torque TP can be obtained by multiplying the slippage s by a proportional coefficient KP. Based on the driving torque TB of the engine 2 and the correction torques TI and TP obtained from equations (2), (5) and (6), a calculation formula for the first target torque TOS(n) may be given as follows:

$$TOS(n)=(TB-TI-TP+TR)/(\rho m \cdot \rho d),$$

where ρm is the change gear ratio of a transmission (not shown), and ρd is the reduction gear ratio of differential gears. When the first target torque TOS(n) is calculated in Step S401, as mentioned before, the processes of Step S402 and its subsequent steps are executed on condition that the first manual switch 132 (see FIG. 2) is on. Thus, the first manual switch 132 is a switch for manually starting the slip control. Here it is to be noted that Step S401 is executed without regard to the activation of the switch 132.

When the program proceeds to Step S402 on the assumption that the first manual switch 132 is on, it is determined whether or not a control flag FS is set. Since the control flag FS is not set yet in this case, the result of decision in Step S402 is NO, whereupon the program proceeds to Step S403. In Step S403, it is determined whether or not the slippage s is greater than a preset threshold value, e.g., 2 km/h. If the decision in Step S403 is YES, it is determined in Step S404 whether or not a changing rate GS of the slippage s is greater than 0.2 g. If the decision in Step S404 is YES, the control flag FS is set in Step S405. The changing rate GS of the slippage s can be obtained from the difference between a slippage s(n) calculated this time and a slippage s(n−1) calculated in the preceding cycle.

In Step S406, it is determined whether or not the control flag FS is set, as in the case of Step S402. If the decision in Step S406 is YES, the first target torque TOS(n) calculated in Step S401 is set as the first target torque TOS in Step S407. If the result of decision in Step S406 is NO, on the other hand, the program proceeds to Step S408, whereupon the maximum driving torque TM of the engine 2 is set as the first target torque TOS.

When the maximum torque TM of the engine 2 is supplied, as the first target torque TOS, from the TCL 112 to the ECU 104, the ECU lowers the respective duty factors of the first and second solenoid valves 80 and 94 to predetermined values on the 0% side. In this case, the engine 2 can produce a driving torque corresponding to the depth of depression of the accelerator pedal 44 by the driver.

It is for the purpose of ensuring the stability of the slip control that the maximum driving torque TM of the engine 2 is set as the first target torque TOS in Step S408. Thus, when Step S408 is executed, the ECU 104 acts so as to de-energize the respective solenoids of the first and second solenoid valves 80 and 94, so that the throttle valve 12 of the engine 2 is mechanically actuated depending on the depression of the accelerator pedal 44. In this manner, the driving torque of the engine 2 can be securely controlled at the driver's will.

If the result of decision in Step S403 or S404 is NO, that is, if the slippage s is smaller than 2 km/h or if the changing rate GS of the slippage s is lower than 0.2 g, the program proceeds to Step S408 via Step S405, whereupon the maximum driving torque TM of the engine 2 is set as the first target torque TOS.

If the result of decision in Step S402 becomes YES as the arithmetic routine of Step S400 is repeatedly executed, that is, after Step S405 is already executed, the program proceeds to Step S409. In Step S409, it is determined whether or not the idle switch 110 is on. If the decision in Step S409 is YES, then it indicates that the accelerator pedal 44 is not depressed, so that the control flag FS is reset in Step S410, whereupon the program proceeds to Step S406. If the result of decision in Step S409 is NO, however, the program proceeds directly to Step S406.

Figure 17:
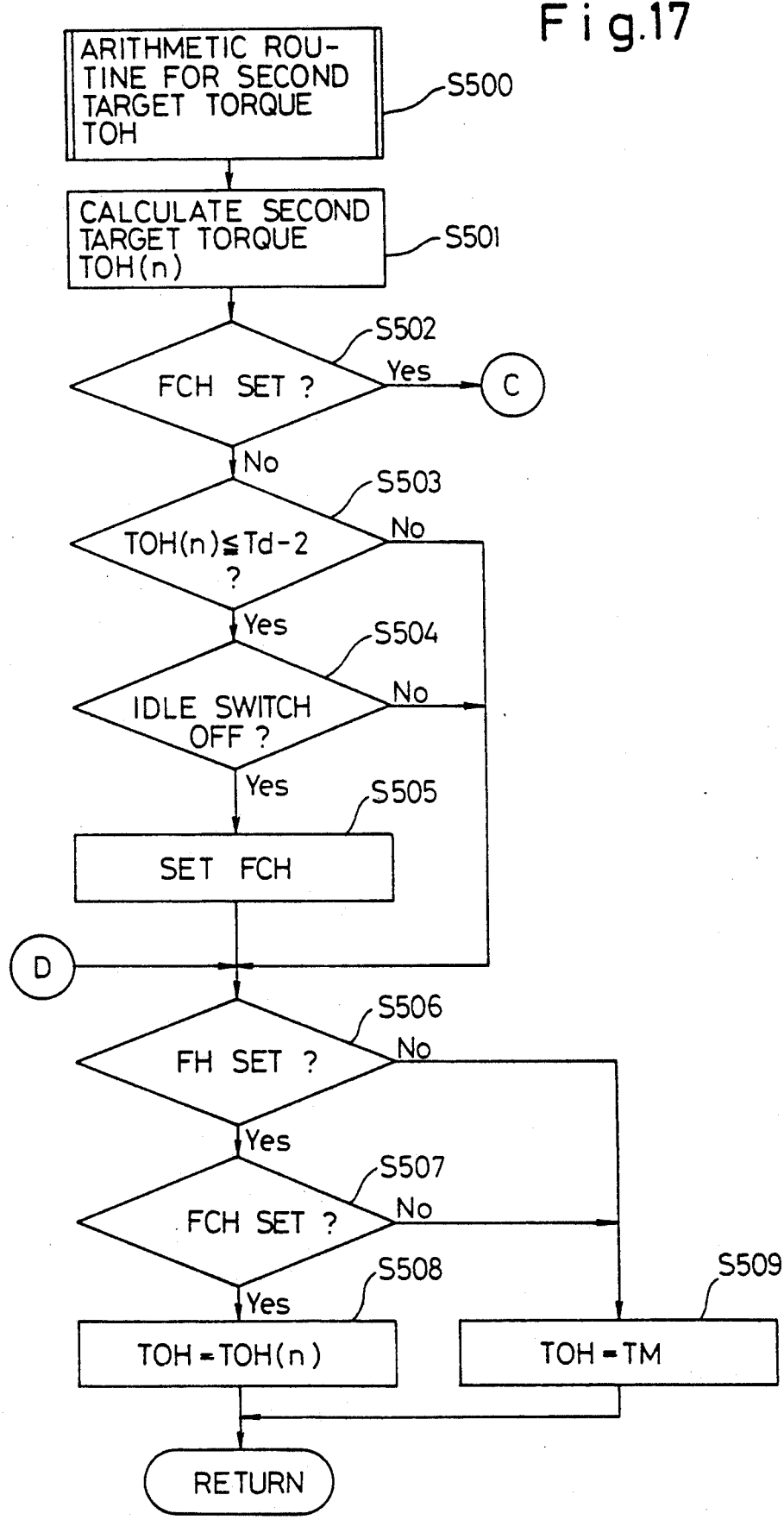
FIGS. 17 and 18 are flow charts showing the detail of an arithmetic routine for a second target torque shown in FIG. 9.
Figure 18:
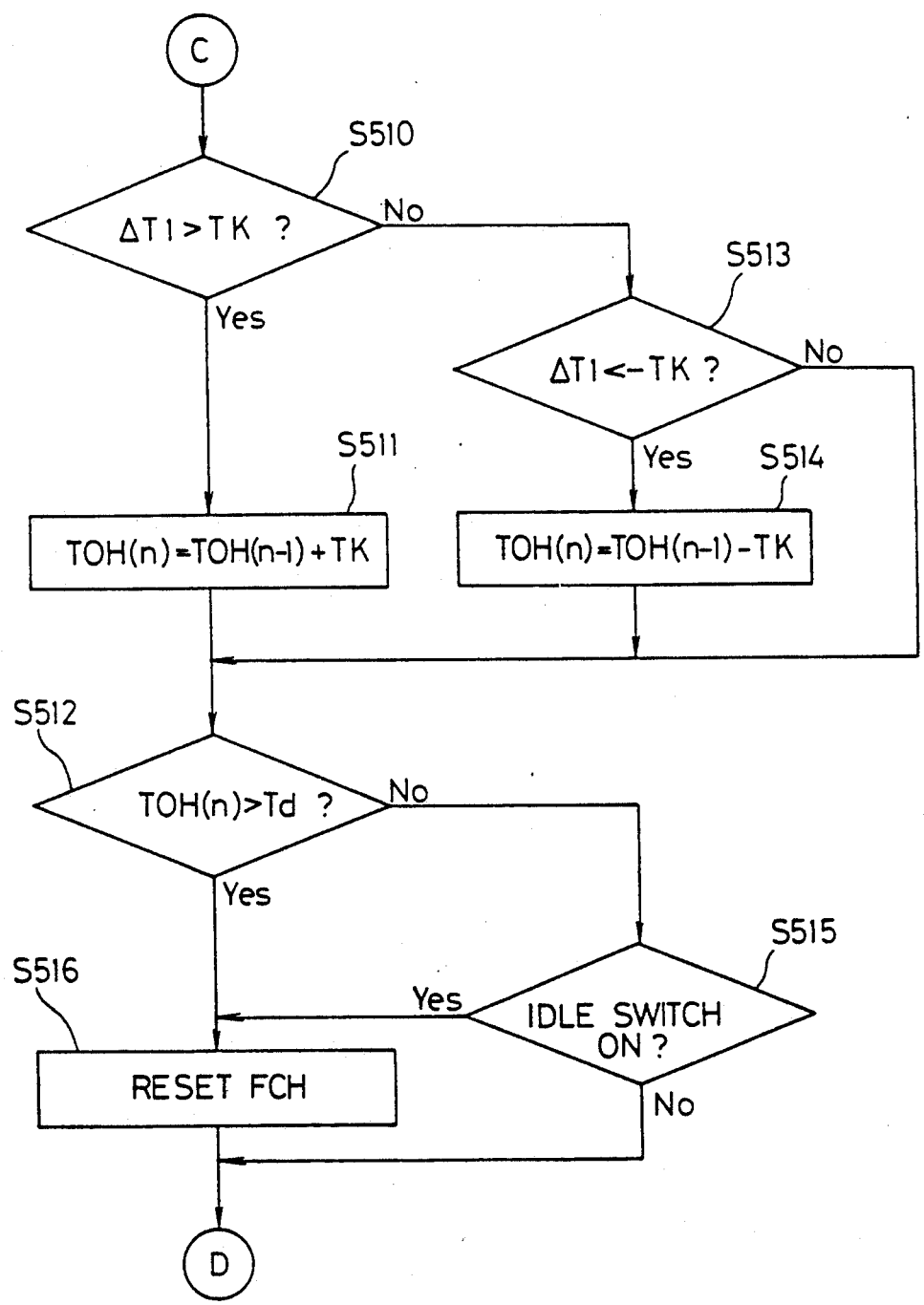

When the program returns to the main calculation routine of FIG. 9 after the execution of the aforementioned arithmetic routine for the first target torque TOS, an arithmetic routine for a second target torque TOH, which is used for the turning control for the case of the high-μ road, is then executed. FIGS. 17 and 18 show the detail of this arithmetic routine. Referring now to FIGS. 17 and 18, the arithmetic routine for the second target torque TOH will be described.

Arithmetic Routine for Second Target Torque TOH

Figure 19:
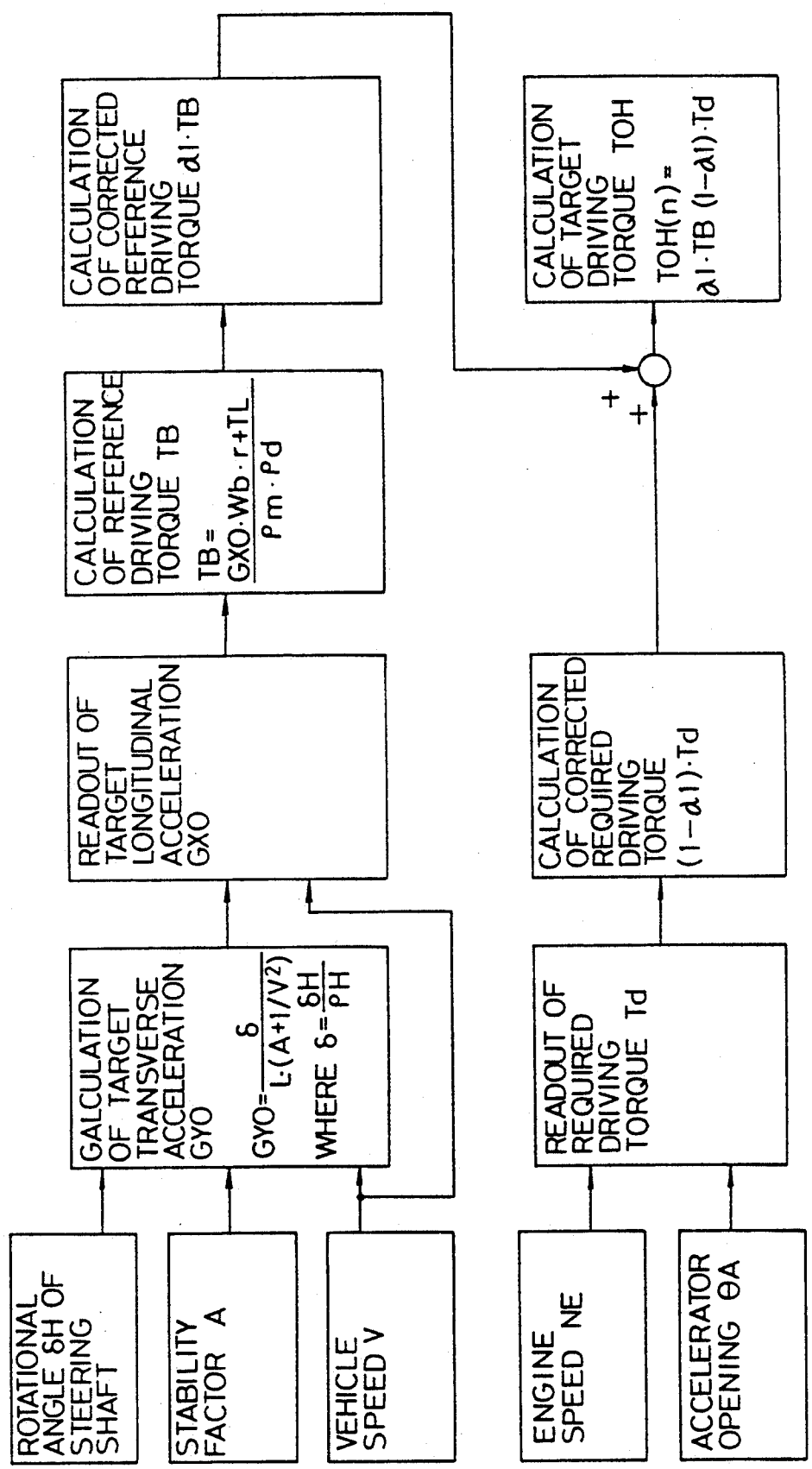
FIG. 19 is a block diagram showing the procedure of calculation followed in a first step of FIG. 17.

A second target torque TOH(n) for the present point of time is calculated in Step S501. FIG. 19 shows the procedure of calculation of the second target torque TOH(n). Before describing the process of Step 502 and the subsequent steps of FIGS. 17 and 18, the procedure of calculation of the second target torque TOH(n) with reference to the block diagram of FIG. 19. As seen from FIG. 19, the rotational angle δH of the steering shaft 128, stability factor A, and vehicle speed V are first obtained individually. Since this arithmetic routine is intended for the case of a high-μ road, the stability factor A is set at 0.002 or less, as described before with reference to the graph of FIG. 6. When the rotational angle δH of the steering shaft 128 is read, the steering angle δ of the front wheels FW is calculated according to the following equation.

$$\delta = \delta H / \rho H. \qquad (8)$$

In this connection, the target transverse acceleration GYO of the vehicle can be calculated as follows:

$$GYO = \delta / \{L \cdot (A + 1/V^2)\} \qquad (9)$$

If the target transverse acceleration GYO exceeds 0.6 g, the stability factor A suddenly increases, as described in connection with the graph of FIGS. 6 and 7. When controlling the driving torque of the engine 2 in accordance with the second target torque TOH, therefore, the second target torque TOH should be set so that the target transverse acceleration GYO calculated according to equation (9) is less than 0.6 g. The target transverse acceleration GYO may be also calculated in accordance with the aforementioned rear-wheel speed difference |VRL−VRR|. As in the case of this embodiment, however, the responsiveness of the turning control can be improved by calculating or estimating the target transverse acceleration GYO in accordance with the rotational angle δH of the steering shaft 128.

Figure 20:
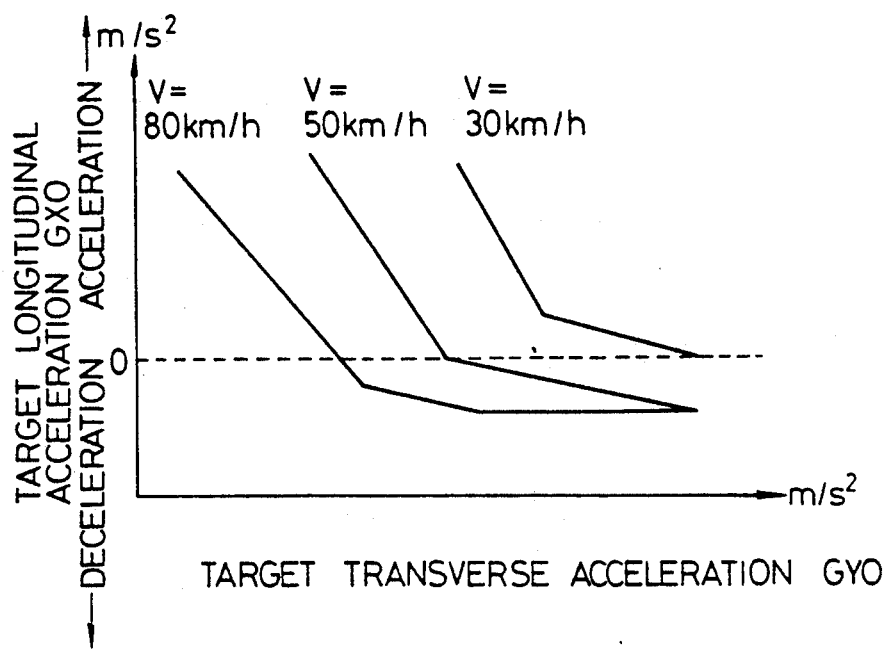
FIG. 20 is a graph showing the relationships between a target transverse acceleration and a target longitudinal acceleration associated with the arithmetic routine of FIG. 17.
Figure 21:
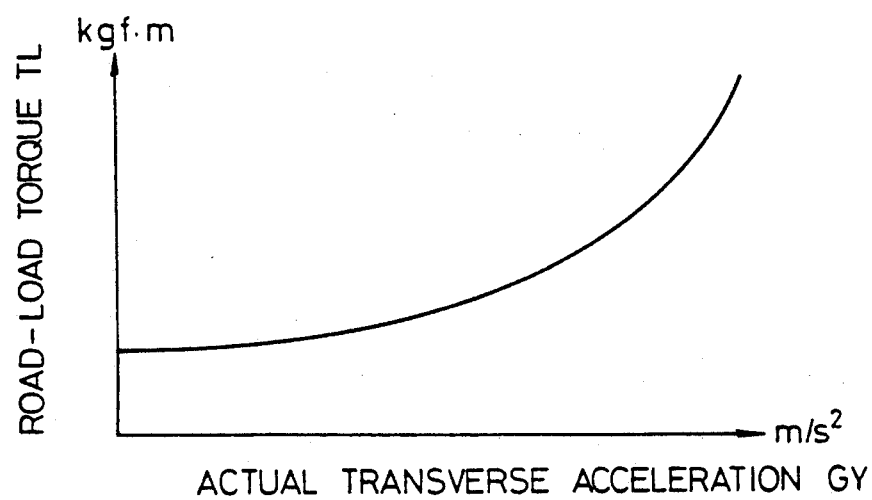
FIG. 21 is a graph showing the relationship between the actual transverse acceleration and roadload torque.
Figure 22:
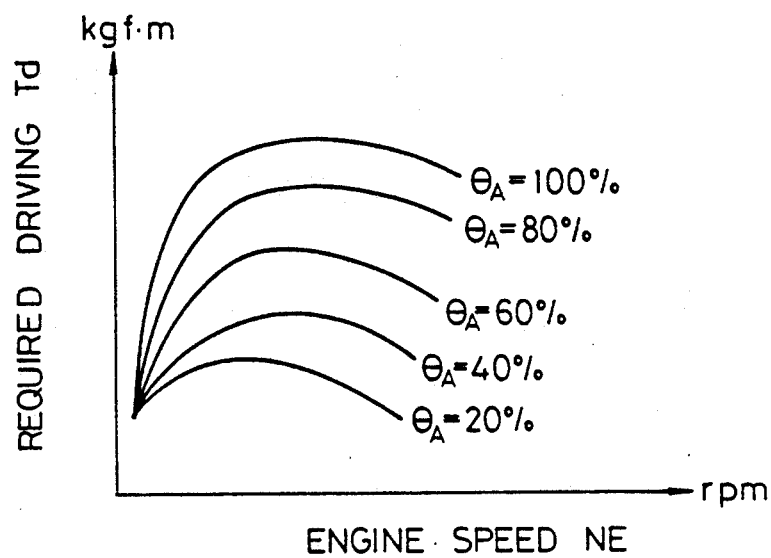
FIG. 22 is a graph showing the relationships between the engine speed and the driving torque of the engine required by a driver.

When the target transverse acceleration GYO is calculated, the target longitudinal acceleration GXO of the vehicle is then obtained in accordance with the value GYO. More specifically, the target longitudinal acceleration GXO compared with the target transverse acceleration GYO is previously obtained according to the vehicle speed V, as shown in the map of FIG. 20. Thus, based on this map, the target longitudinal acceleration GXO is read in accordance with the target transverse acceleration GYO and the vehicle speed V. When the target longitudinal acceleration GXO is obtained in this manner, the reference driving torque TB of the engine 2 is calculated according to the following equation using the value GXO.

$$TB = (GXO \cdot Wb \cdot r + TL)/(\rho m \cdot \rho d), \qquad (10)$$

where TL is road-load torque, which can be obtained corresponding to the actual transverse acceleration GY from the map of FIG. 21.

Then, the reference driving torque TB is multiplied by a weighting factor $\alpha 1$, whereby a corrected reference driving torque ($=\alpha 1 \cdot TB$) is calculated. The weighting factor $\alpha 1$, which is empirically set depending on the results of vehicle turning tests, is adjusted to 0.6 or thereabout for the case of a high-$\mu$ road.

Meanwhile, a required driving torque Td is calculated according to the engine speed NE, obtained in response to the detection signal from the crank angle sensor 106, and an accelerator opening $\theta A$ obtained in response to the detection signal from the accelerator opening sensor 116. The required driving torque Td is a driving torque which is supposed to be required of the engine 2 by the driver. The required driving torque Td is also multiplied by a weighting factor $(1-\alpha 1)$, whereby a corrected required driving torque $(1-\alpha 1) \cdot Td$ is calculated.

When the reference driving torque $\alpha 1 \cdot TB$ and the required driving torque $(1-\alpha 1) \cdot Td$, corrected by their corresponding weighting factors, are obtained in this manner, these two values are added together to obtain the second target torque TOH(n) for the present point of time. Thus, the second target torque TOH(n) is calculated as follows:

$$TOH(n) = \alpha 1 \cdot TB + (1-\alpha 1) \cdot Td. \qquad (11)$$

If the weighting factor $\alpha 1$ is set at 0.6, the ratio of the reference driving torque TB and the required driving torque Td to the second target torque TOH(n) is 6:4.

When Step S501 of FIG. 17 is executed with reference to the block diagram of FIG. 19 so that the second target torque TOH(n) is calculated, the program then proceeds to Step S502 and its subsequent steps, which are executed on condition that the second manual switch 134 (see FIG. 2) is on.

First, in Step S502, it is determined whether or not a control flag FCH is set. The control flag FCH is a flag which indicates whether or not the vehicle is under high-$\mu$ road turning control. If this arithmetic routine is executed for the first time, the control flag FCH is not set yet, so that the result of decision in Step S502 is NO, whereupon the program proceeds to Step S503. In Step S503, it is determined whether or not the second target torque TOH(n) is not greater than a preset threshold value, e.g., (Td−2). As mentioned before, Td is the required driving torque of the engine 2. The process of Step S503 is needed for the following reason. The second target torque TOH(n) for the turning control can be calculated even while the vehicle is advancing straight. Usually, however, the second target torque TOH(n) for this case is much greater than the require driving torque Td. More specifically, the target transverse acceleration GYO also takes a small value when the vehicle is advancing straight. In this case, the target longitudinal acceleration GXO of the vehicle read from the map of FIG. 20 is adjusted to a great value based on the target transverse acceleration GYO. Thus, the reference driving torque TB, which is calculated on the basis of the target longitudinal acceleration GXO, takes a great value, so that the second target torque TOH(n) is greater than the required driving torque Td, in general. While the vehicle is turning, on the other hand, the target transverse acceleration GYO takes a great value, so that the target longitudinal acceleration GXO is small. In general, therefore, the reference driving torque TB calculated on the basis of the target longitudinal acceleration GXO, that is, the second target torque TOH(n), is smaller than the required driving torque Td. Thus, by executing the process of Step S503, it can be determined whether or not the requirements for the start of the turning control is fulfilled.

The value (Td−2), not Td, is set as the threshold value because the difference between Td and (Td−2) functions as hysteresis for preventing hunting with relation to the start of the turning control.

If the decision in Step S503 is YES, it is then determined in Step S504 whether or not the idle switch 110 is off. If the decision in Step S504 is YES, that is, if the accelerator pedal 44 is depressed, the control flag FCH is set in Step S505, whereupon the program proceeds to Step S506. In Step S506, it is determined whether or not the flag FH is set. Since the control flag FH indicates whether or not the learning correction of the neutral position $\delta M$ of the steering shaft 128 is already executed, as described in connection with the learning routine of FIGS. 10 and 11, the reliability of the value of the steering angle $\delta$ obtained in response to the detection signal from the steering angle sensor 126 can be determined by executing Step S506. If the decision in Step S506 is YES, it is determined again in Step S507 whether or not the control flag FCH is set. In this case, the control flag FCH is already set in Step S505, that is, the result of decision in Step S507 is YES, so that the program proceeds to Step S508. In Step S508, the second target torque TOH(n) already calculated in Step S501 is set directly as the second target torque TOH.

If the result of decision in Step S506 is NO, on the other hand, the value of the steering angle $\delta$ of the front wheels FW calculated according to equation (8) can be determined to be unreliable, so that the value of the second target torque TOH(n), which is calculated according to equations (9), (10) and (11) based on the steering angle $\delta$, is also unreliable. In this case, therefore, the program proceeds to Step S509, whereupon the maximum driving torque TM of the engine 2 is set as the second target torque TOH. Also in this case, if the second target torque TOH adjusted to the maximum driving torque TM is supplied from the TCL 112 to the ECU 104, the ECU set the respective duty factors of the first and second solenoid valves 80 and 94 at predetermined values on the 0% side. Thus, the driving torque of the engine 2 depends on the depth of depression of the accelerator pedal 44 by the driver.

If the result of decision in Step S503 is NO, the program proceeds directly to Step S506, skipping Steps S504 and S505. In this case, the result of decision in Step S506 or S507 is NO, so that the program proceeds to Step S509. If the result of decision in Step S504 is NO, the program also proceeds to Step S509 via Step S506 or S507, so that the engine 2 produces the driving torque corresponding to the depth of depression of the accelerator pedal 44. If the arithmetic routine of FIGS. 17 and 18 are repeatedly executed after Step S505 is executed, the result of decision in Step S502 is YES, so that the program proceeds to Step S510 shown in FIG. 18, whereupon Step S510 and its subsequent steps are executed. In Step S510, it is determined whether or not a torque deviation $\Delta T1$ is greater than a preset allowable value TK. The torque deviation $\Delta T1$ is a deviation between the second target torque TOH(n) calculated this time and a second target torque TOH(n−1) calculated in the preceding cycle. The allowable value Tk represents the maximum variation of the driving torque of the engine 2 that cannot give an acceleration or deceleration shock to the occupants of the vehicle. If the target longitudinal acceleration GXO of the vehicle is restricted to 0.1 g/s, for example, the allowable value TK can be calculated according to the following equation based on equation (10).

$$TK = 0.1 \cdot (Wb \cdot r) \cdot \Delta t / (\rho m \cdot pd).$$

If the result of decision in Step S510 is YES, the second target torque TOH(n) calculated this time is recalculated according to the following equation in Step S511, whereupon the program proceeds to Step S512.

$$TOH(n) = TOH(n-1) + TK.$$

If the result of decision in Step S510 is NO, on the other hand, the program proceeds to Step S513, whereupon it is determined whether or not the torque deviation ΔT1 is smaller than a negative allowable value TK. If the decision in Step S513 is YES, the second target torque TOH(n) calculated this time is recalculated according to the following equation in Step S514, whereupon the program proceeds to Step S512.

$$TOH(n) = TOH(n-1) - TK.$$

If both the results of decision in Steps S510 and S513 are NO, that is, if the absolute value |ΔT1| of the torque deviation ΔT1 is smaller than the allowable value TK, the program proceeds directly to Step S512, skipping Steps S511 and S514.

If the torque deviation ΔT1 exceeds the allowable value TK, therefore, the second target torque TOH(n) calculated this time is restricted to a value obtained by adding the allowable value TK to the preceding second target torque TOH(n−1). Thus, the acceleration shock of the vehicle accompanying the increase of the driving torque of the engine 2 can be reduced. If the torque deviation ΔT1 is smaller than the allowable value −TK, moreover, the second target torque TOH(n) calculated this time is restricted to a value obtained by subtracting the allowable value TK from the preceding second target torque TOH(n−1), so that the deceleration shock of the vehicle accompanying the reduction of the driving torque of the engine 2 can be also reduced. If the absolute value of the torque deviation ΔT1 is smaller than the allowable value TK, furthermore, the second target torque TOH(n) calculated in Step S501 is delivered to the subsequent steps.

Figure 23:
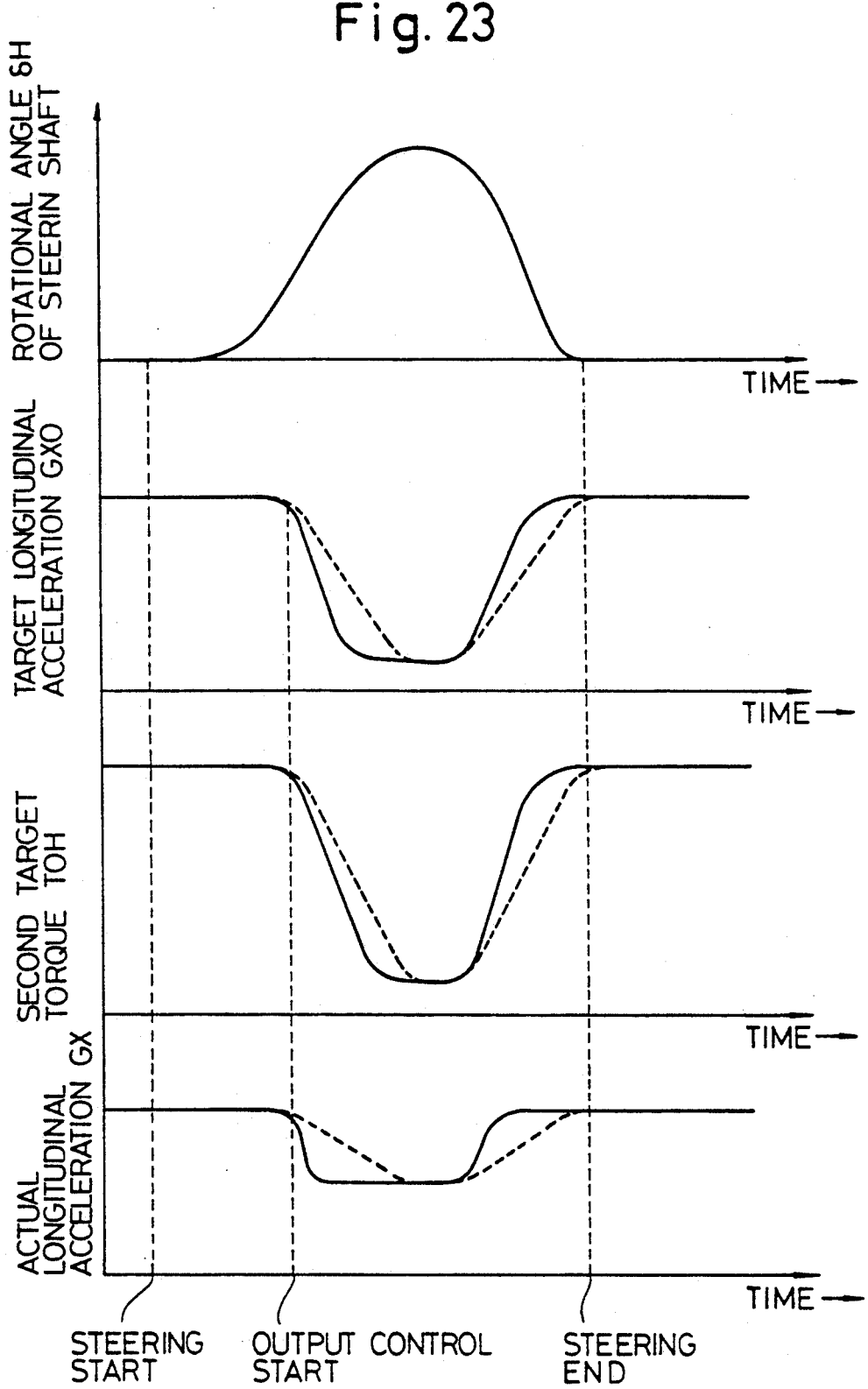
FIG. 23 is a graph showing time-based transitions of the rotational angle of a steering shaft, target longitudinal acceleration, second target torque, and actual longitudinal acceleration obtained when the arithmetic routine of FIG. 17 is executed.

As seen from FIG. 23, it is advantageous that the correction amount of the second target torque TOH(n) is restricted to the absolute value of the torque deviation ΔT1 by executing Step S511 or S514 even though the result of decision in Step S510 or S513 is YES. In FIG. 23, full-line curves represent time-based transitions of the rotational angle δH of the steering shaft 128, target longitudinal acceleration GXO, second target torque TOH, and actual longitudinal acceleration GX, obtained without the execution of Step S511 and S514, while broken-line curves represent time-based transitions of the target longitudinal acceleration GXO, second target torque TOH, and actual longitudinal acceleration GX, obtained the execution of Steps S511 and S514. Thus, as seen from FIG. 23, the transition of the actual longitudinal acceleration GX indicated by the broken-line curve is smoother than that of the actual longitudinal acceleration GX indicated by the full-line curve, so that the acceleration or deceleration shock is effectively reduced.

In Step S512, it is determined whether or not the second target torque TOH(n) is greater than the required driving torque Td. If the control flag FCH is set at this point of time, the second target torque TOH(n) cannot be greater than the required driving torque Td, as is evident from the foregoing description, so that the result of decision in Step S512 is NO, whereupon the program proceeds to Step S515. In Step S515, it is determined whether or not the idle switch 110 is on. If the result of decision in Step S515 is NO, it is concluded that the turning control is required, whereupon the program proceeds to Step S506 of FIG. 17.

If the result of decision in Step S512 is YES, that is, if the second target torque TOH(n) is greater than the required driving torque Td, on the other hand, it can be concluded that the turning of the vehicle is finished. In this case, the control flag FCH is reset in Step S516, whereupon the program proceeds to Step S506. If the result of decision in Step S515 is YES, that is, if the accelerator pedal 44 is not depressed, the control flag FCH is also reset in Step S516, and the program then proceeds to Step S506. If Step S506 and its subsequent steps are executed after the control flag FCH is reset, Step S509 never fails to be executed, so that the engine 2 produces the driving torque corresponding to the depth of depression of the accelerator pedal 44.

In the aforementioned arithmetic routine for the second target torque TOH, the second target torque TOH(n) is calculated according to the target transverse acceleration GYO, and the final second target torque TOH for the turning control is decided by comparing the second target torque TOH(n) and the threshold value (Td−2). Alternatively, however, the second target torque TOH may be decided by comparing the target transverse acceleration GYO and a preset reference value (e.g., 0.6 g) and executing Step S504 and its subsequent steps when the reference value is attained or exceeded by the target transverse acceleration GYO.

Figure 24:
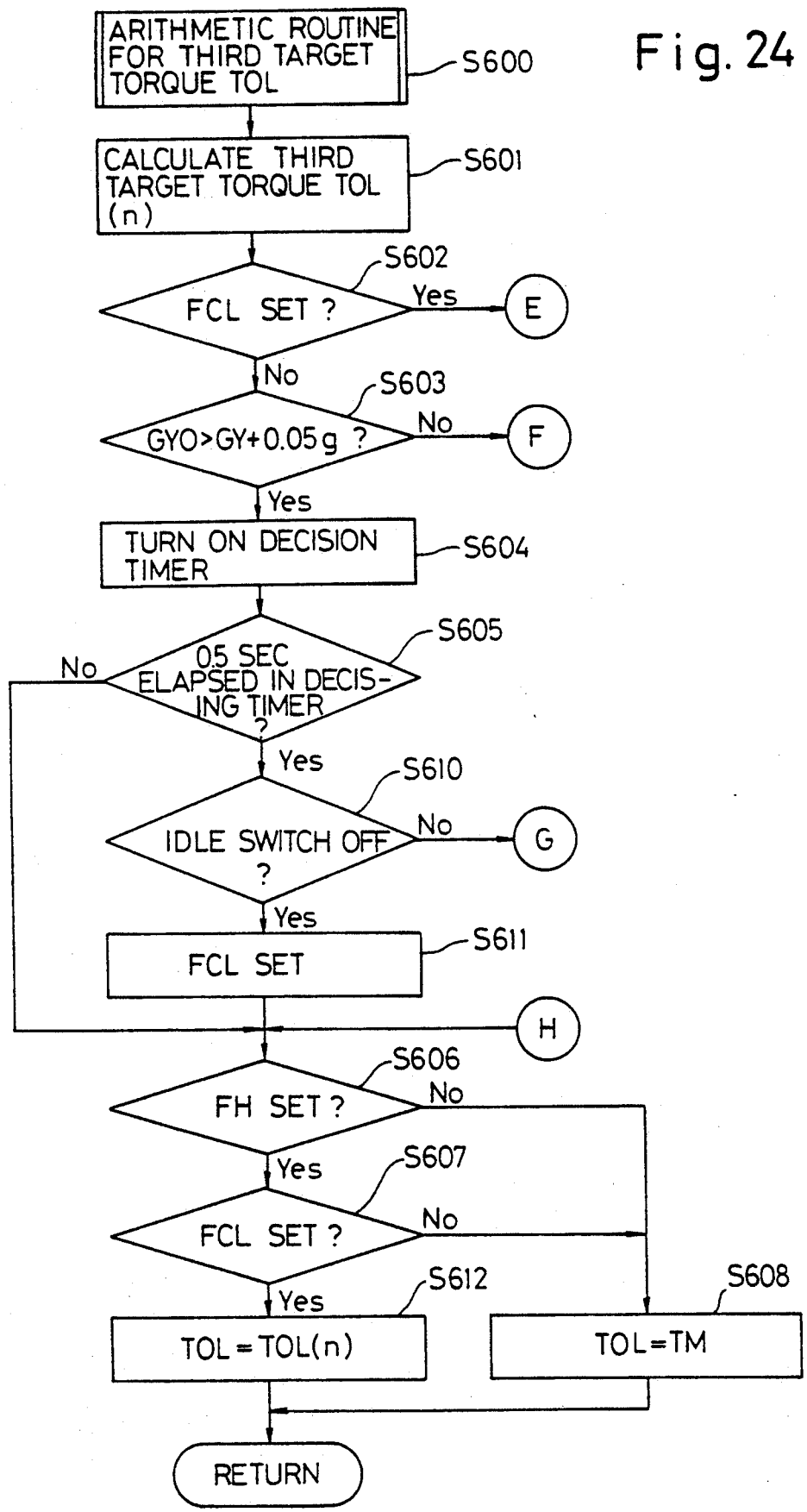
FIGS. 24 and 25 are flow charts showing the detail of an arithmetic routine for a third target torque shown in FIG. 9.
Figure 25:
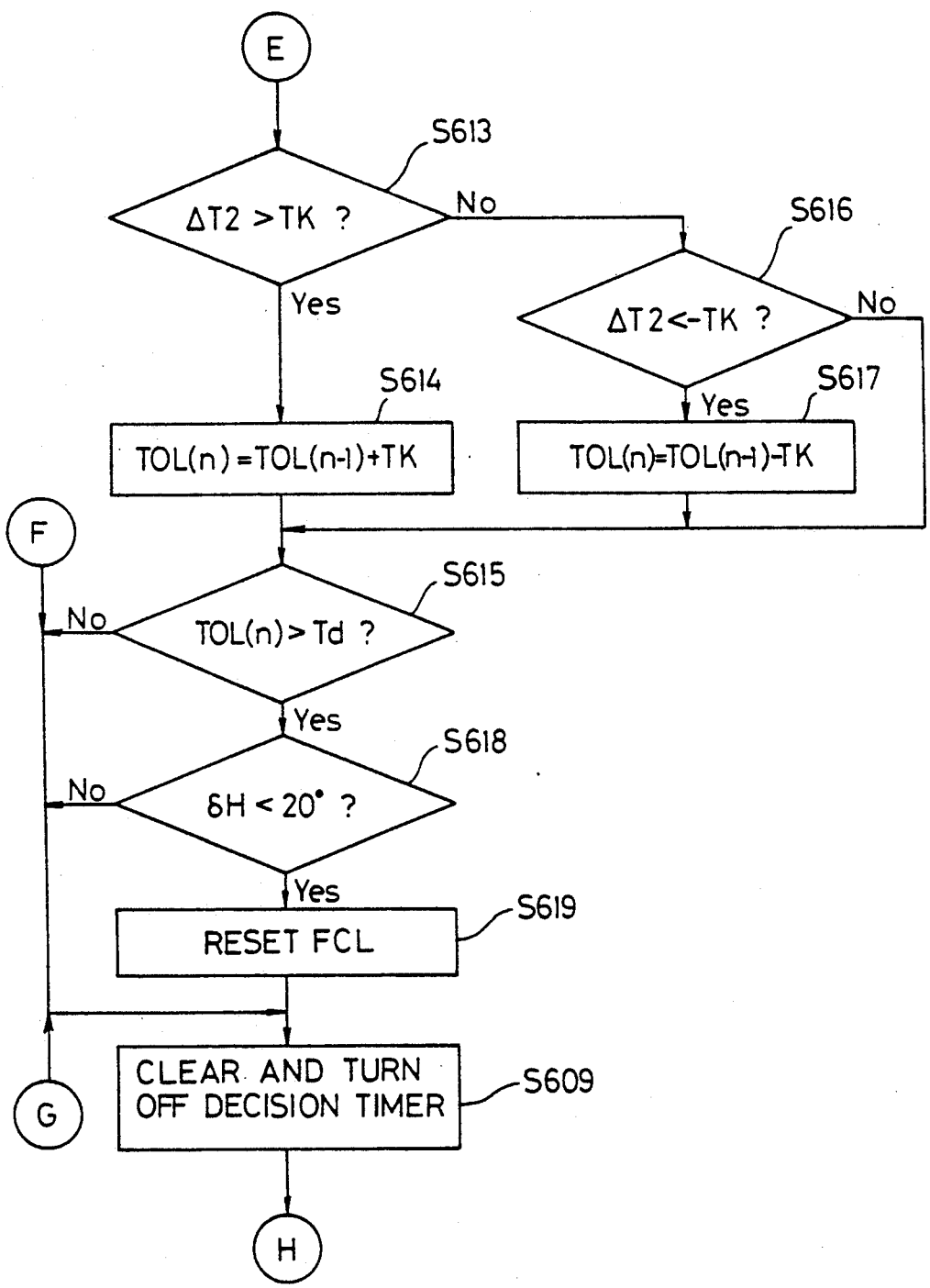

After the arithmetic routine for the second target torque TOH shown in FIGS. 17 and 18 are executed, the program returns to the main calculation routine. In Step S600 of the main calculation routine, the third target torque TOL used for low-μ road turning control is calculated. FIGS. 24 and 25 show the detail of this arithmetic routine. The following is a description of the arithmetic routine for the third target torque TOL.

Arithmetic Routine for Third Target Torque TOL

This arithmetic routine is executed following the same steps of procedure as the foregoing arithmetic routine for the second target torque TOH. More specifically, a third target torque TOL(n) for the present point of time is calculated in Step S601. The procedure of calculation of the third target torque TOL(n) is shown in the block diagram of FIG. 26.

First, the rotational angle δH of the steering shaft 128, stability factor A, and vehicle speed V are first obtained. Since this arithmetic routine is intended for the calculation of the third target torque TOL(n) for the case of a low-μ road, the stability factor A is set at 0.005, for example.

Figure 27:
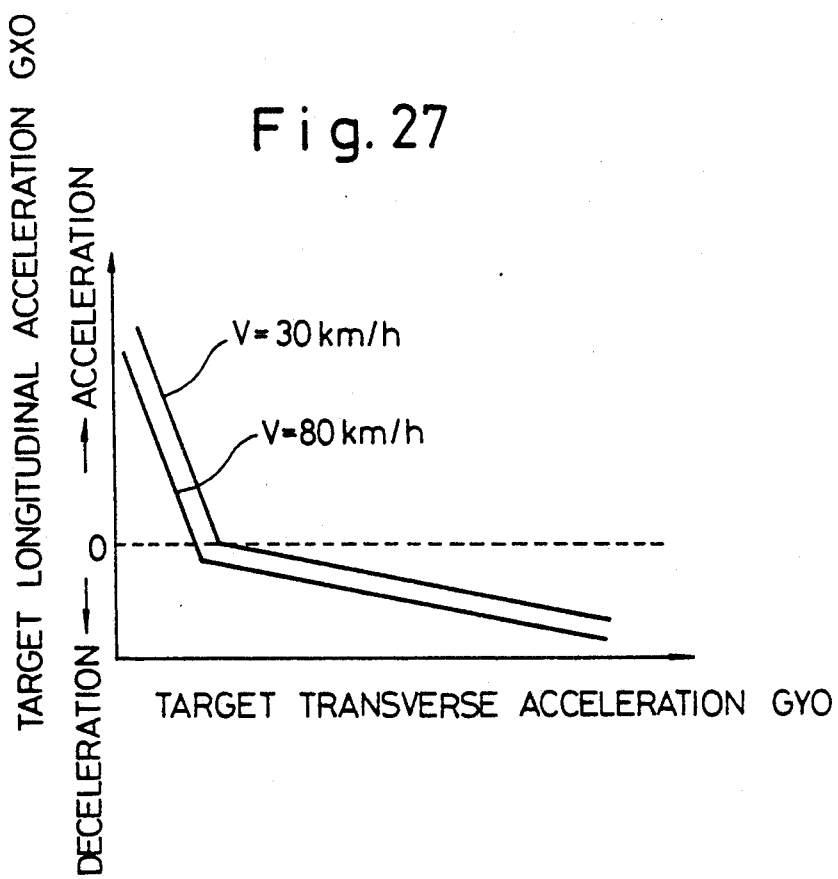
FIG. 27 is a graph showing the relationships between the target transverse acceleration and the target longitudinal acceleration associated with the arithmetic routine of FIG. 24.

Then, the target transverse acceleration GYO is calculated according to equations (8) and (9), and the target longitudinal acceleration GXO is obtained in accordance with the target transverse acceleration GYO and the vehicle speed V. Specifically, the target longitudinal acceleration GXO is read from the map of FIG. 27. In this map, the target longitudinal acceleration GXO which can ensure stable running of the vehicle is represented depending on the target transverse acceleration GYO for each of various vehicle speeds V. The map of FIG. 27 is created in accordance with the results of test runs of the vehicle.

Thereafter, the reference driving torque TB is calculated according to the equation (10) based on the target longitudinal acceleration GXO. Alternatively, the torque TB may be read from a map prepared to indicate the relationship between the target longitudinal acceleration GXO and the reference driving torque TB.

The reference driving torque TB is multiplied by a weighting factor $\alpha 2$, whereby a corrected reference driving torque $\alpha 2 \cdot TB$ is calculated. In this case, the weighting factor $\alpha 2$ is adjusted to a value greater than the weighting factor $\alpha 1$ for the case of a high-$\mu$ road, e.g., 0.8.

Since the required driving torque Td is already calculated in the arithmetic routine for the second target torque TOH for the case of a high-$\mu$ road, the third target torque TOL(n) can be calculated as follows:

$$TOL(n) = \alpha 2 \cdot TB + (1 - \alpha 2) \cdot Td. \quad (12)$$

In calculating the third target torque TOL, the value of the weighting factor $\alpha 2$ is greater than the value of the weighting factor $\alpha 1$ for the case of a high-$\mu$ road, so that the ratio of the reference driving torque TB to the third target torque TOL is higher than the ratio to the second target torque TOH, while the ratio of the required driving torque Td is lower. If the ratio of the required driving torque Td to the third target torque TOL is thus lowered in the case of a low-$\mu$ road, the vehicle can turn more stably and securely on the low-$\mu$ road.

When Step S601 is executed, the program proceeds to Step S602 and its subsequent steps, which are executed on condition that the third manual switch 136 (see FIG. 2) is on.

Figure 26:
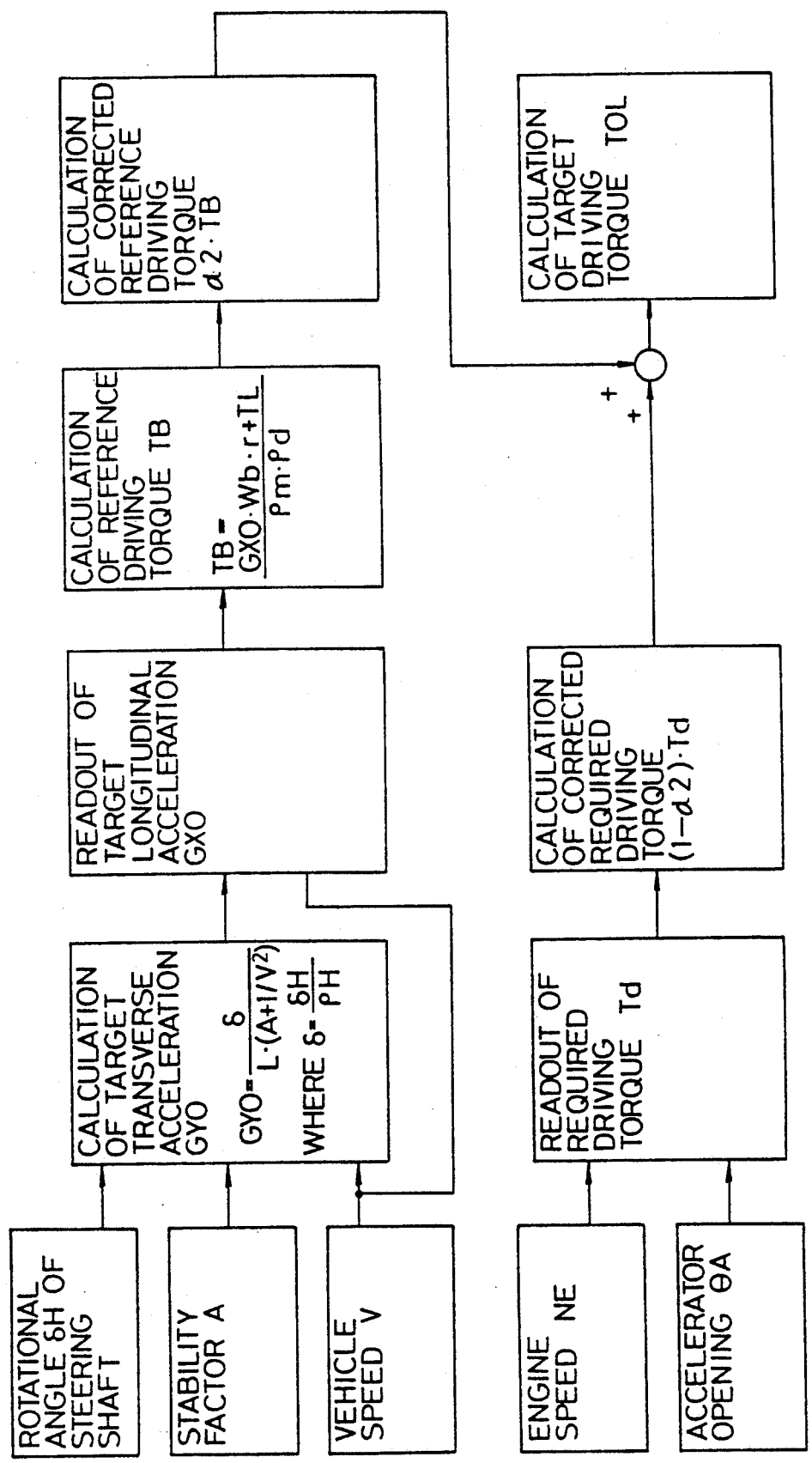
FIG. 26 is a block diagram showing the procedure of calculation followed in a first step of FIG. 24.

In Step S602, it is determined whether or not a control flag FCL is set. The control flag FCL is a flag which indicates whether or not the vehicle is under the low-$\mu$ road turning control. If the arithmetic routine of FIGS. 25 and 26 are executed for the first time, the control flag FCL is not set yet, so that the decision in Step S602 is NO, whereupon the program proceeds to Step S603.

In Step S603, it is determined whether or not the following relation holds.

$$GYO > GY + 0.5 \text{ g},$$

where GY indicates the actual transverse acceleration of the vehicle detected by means of the linear G sensor 130, as mentioned before, and the value of 0.05 g functions as hysteresis for preventing hunting associated with the decision in Step S603.

If the result of decision in Step S603 is YES, then it can be concluded in this case that the vehicle is turning on a low-$\mu$ road, and the program proceeds to Step S604. In Step S604, the operation of a built-in decision timer contained in the TCL 112 is started, it is then determined in Step S605 whether or not 0.5 sec is attained by the value in the decision timer. Immediately after Step S604 is executed, the decision in Step S605 is NO, so that the program proceeds to Step S606, whereupon Step S606 and its subsequent steps are executed. In Step S606, it is determined whether or not the learning flag FH is set. Then, in Step S607, it is determined whether or not the control flag FCL is set. At this point of time, the result of decision in Step S607 is NO, without regard to the result of decision in Step S606, so that Step S608 never fails to be executed. The decision of Step S606 is needed for the same reason as the decision of Step S506 of the arithmetic routine of FIGS. 17 and 18.

In Step S608, the maximum driving torque TM of the engine 2 is set as the third target torque TOL. Thus, when the maximum torque TM of the engine 2 is supplied, as the third target torque TOL, from the TCL 112 to the ECU 104, the ECU sets the respective duty factors of the first and second solenoid valves 80 and 94 at predetermined values on the 0% side. In this case, the engine 2 can produce a driving torque corresponding to the depth of depression of the accelerator pedal 44 by the driver. Step S608 continues to be executed until both the results of decision in Steps S603 and S605 become YES.

If the result of decision in Step S603 becomes NO before the decision in Step S605 becomes YES as the arithmetic routine of FIG. 25 is repeatedly executed, thereafter, it can be concluded that the vehicle is not turning on a low-$\mu$ road, so that the program proceeds to Step S609. In Step S609, the value in the decision timer is cleared, and the operation of this timer is stopped, whereupon Step S606 and its subsequent steps are executed in like manner. The decision in Step S606 of the arithmetic routine of FIG. 25 is substantially the same as the decision in Step S2 of the low-$\mu$ road decision routine described with reference to FIG. 5. It is to be understood, however, that the low-$\mu$ road decision can be effected by using a process similar to Step S6 of FIG. 5 in place of Step S2 or S603.

If the result of decision in Step S605 becomes YES with the result of decision in Step S603 kept YES, that is, if the state in which the running road is determined to be a low-$\mu$ road in Step S603 continues for 0.5 sec, the program then proceeds to Step S610, whereupon it is determined whether or not the idle switch 110 is off. If the result of decision in Step S610 is NO, that is, if the accelerator pedal 44 is not depressed, the program proceeds to Step S606 and its subsequent steps via Step S609. Thus, even in these circumstances, the engine 2 produces a driving torque corresponding to the depth of depression of the accelerator pedal 44, as is evident from the above description.

If the result of decision in Step S610 is YES with the accelerator pedal 44 depressed, however, the control flag FCL is set in Step S611.

If Step S606 and its subsequent steps are executed after the execution of Step S611, the program proceeds to Step S612 on condition that the result of decision in Step S606 is YES. In Step S612, the third target torque TOL(n) for the present point of time is set directly as the third target torque TOL. If the result of decision in Step S606 is NO, Step S608 is executed even though the control flag FCL is set, so that the engine 2 produces a driving torque corresponding to the depth of depression of the accelerator pedal 44.

If this arithmetic routine is repeatedly executed after the control flag FCL is set in Step S611, the decision in Step S602 becomes YES, so that the program proceeds to Step S613 of FIG. 26 and its subsequent steps. In Step S613, it is determined whether or not a torque deviation ΔT2 is greater than the aforementioned allowable value TK. The torque deviation ΔT2 indicates the difference between the third target torque TOL(n) calculated this time and a preceding third target torque TOL(n−1).

If the result of decision in Step S613 is YES, the present third target torque TOL(n) is recalculated according to the following equation using the preceding third target torque TOL(n−1) in Step S614, whereupon the program proceeds to Step S615.

$$TOL(n) = TOL(n-1) + TK.$$

If the result of decision in Step S613 is NO, on the other hand, it is determined in Step S616 whether or not the torque deviation ΔT2 is smaller than the negative allowable value −TK. If the result of decision in Step S616 is YES, the present third target torque TOL(n) is recalculated according to the following equation using the preceding third target torque TOL(n−1) in Step S617, whereupon the program proceeds to Step S615.

$$TOL(n) = TOL(n-1) - TK.$$

If the result of decision in Step S616 is NO, the program proceeds directly to Step S615, skipping Steps S614 and S617.

If the absolute value of the deviation ΔT2 is greater than the allowable value TK, therefore, the third target torque TOL(n) calculated this time is restricted to a value obtained by adding or subtracting the allowable value TK to or from the value calculated in the preceding cycle. Then, in Step S615, it is determined whether or not the present third target torque TOL(n) is greater than the required driving torque Td. If the control flag FCL is set, in this case, the third target torque TOL(n) is not greater than the required driving torque Td, so that the result of decision in Step S615 is NO, whereupon the program proceeds to Step S609 and its subsequent steps.

If the result of decision in Step S618 is NO, that is, if the rotational angle δH of the steering shaft 128 is not smaller than 20°, for example, even though the decision in Step S615 is YES, that is, Step S609 and its subsequent steps continue to be executed.

If the result of decision in Step S618 is YES, however, it indicates the end of the vehicle turning, so that the control flag FCL is reset in Step S619, and the program then proceeds to Step S609 and its subsequent steps.

When the control flag FCL is reset, Step S608 never fails to be executed following Step S607 without regard to the result of decision in Step S606, as is evident from the foregoing description, so that the engine 2 produces a driving torque corresponding to the depth of depression of the accelerator pedal 44.

In calculating the second and third target torques TOH(n) and TOL(n) in the arithmetic routines, the reference driving torque TB calculated according to equation (10) may be set as the second or third target torque TOH(n) or TOL(n) without taking account of the required driving torque Td.

Figure 28:
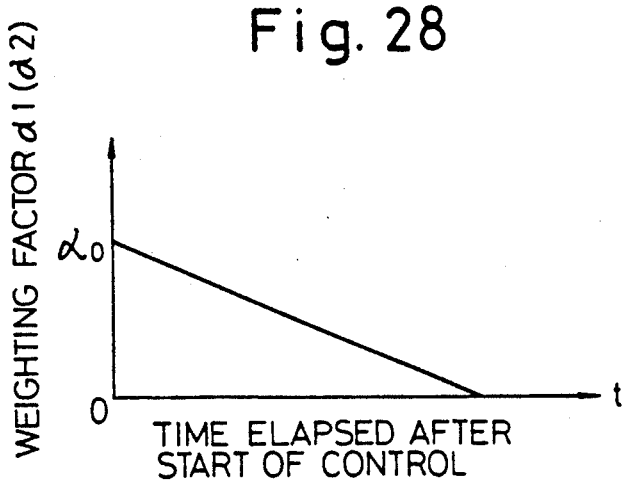
FIGS. 28, 29 and 30 are graphs showing cases in which weighting factors are varied with the passage of time for vehicle turning control in association with the arithmetic routines of FIGS. 17 and 24.
Figure 29:
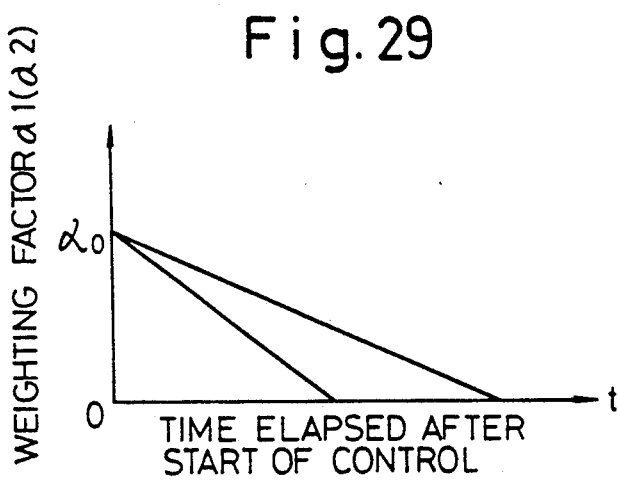
Figure 30:
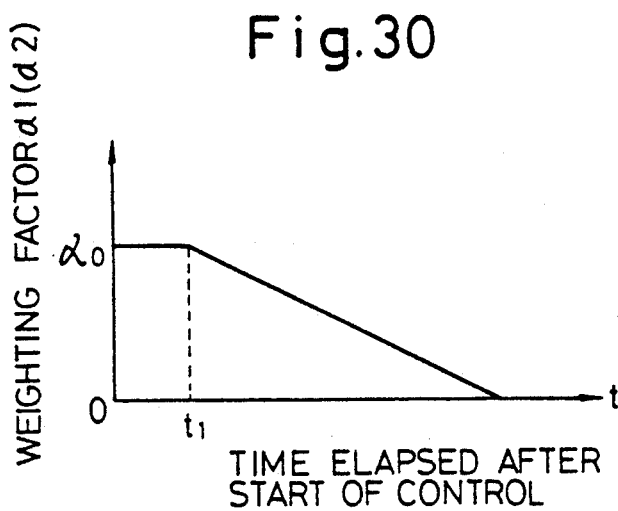

In calculating the second and third target torques TOH(n) and TOL(n) according to the embodiment described above, moreover, the weighting factors α1 and α2 used are constant values. These weighting factors α1 and α2 may, however, be set in various other manners. Referring to FIG. 28, for example, the weighting factor α1 (or α2) is gradually decreased with the passage of time after the start of the turning control, that is, after the start of the main calculation routine. Referring further to FIG. 29, the decreasing rate of the weighting factor α1 (or α2) varies depending on the vehicle speed V with the passage of time. Referring to FIG. 30, furthermore, the weighting factor α1 (or α2) is decreased with the passage of time, although it is kept at a constant value for some time after the start of the main calculation routine. If the value of the weighting factor α1 (or α2) is made greater as the rotational angle δH of the steering shaft 128 increases, moreover, the running stability of the vehicle can be effectively ensured when the vehicle runs on a turning road whose radius of curvature gradually decreases. As regards the arithmetic routines, the correction amount or variation of each of the second and third target torques TOH(n) and TOL(n) for each cycle is restricted to the allowable value TK, in order to prevent an acceleration or deceleration shock from being caused due to a sudden change of the driving torque of the engine 2. However, the same effect can be obtained by previously limiting the variation of the target longitudinal acceleration GXO for each cycle, instead of using the allowable value TK. In this case, the target longitudinal acceleration GXO can be calculated in the following manner. If an acceleration deviation ΔG between a target longitudinal acceleration GXO(n) calculated this time and a target longitudinal acceleration GXO(n−1) calculated in the preceding cycle is greater than an allowable value GK, the target longitudinal acceleration GXO(n) is restricted to a value calculated as follows:

$$GXO(n) = GXO(n-1) + GK.$$

If the acceleration deviation ΔG is smaller than a negative allowable value −GK, on the other hand, the target longitudinal acceleration GXO(n) is restricted to a value calculated as follows:

$$GXO(n) = GXO(n-1) - GK.$$

It is to be understood that the target longitudinal acceleration GXO is used as it is if the absolute value of acceleration deviation ΔG is smaller than the allowable value GK. If the change of the target longitudinal acceleration GXO is restricted within the range of 0.1 g/s in the case where the sampling time of the main timer is 15 msec, moreover, the allowable value GK can be calculated as follows:

$$GK = 0.1 \cdot \Delta t.$$

When the arithmetic routine for the third target torque TOL is executed, the program returns to the main calculation routine of FIG. 9, whereupon a select-/output routine for the final target driving torque TO is executed in Step S700. Basically, in this routine, one of the first to third target torques TOS, TOH and TOL obtained previously is selected as the final target driving torque TO, and the torque TO is then delivered to the ECU 104. To ensure the stability of the vehicle running, in this case, the smallest of the first to third target torques TOS, TOH and TOL is preferably selected as the target driving torque TO with priority. In general, the first target torque TOS for the slip control is always smaller than the third target torque TOL for the low-μ road turning control. In selecting the target driving torque TO, therefore, the slip control, low-μ road turning control, and high-μ road turning control are checked for start in the order named, and the target torque for the control whose start is discriminated is selected as the final target driving torque TO.

Figure 31:
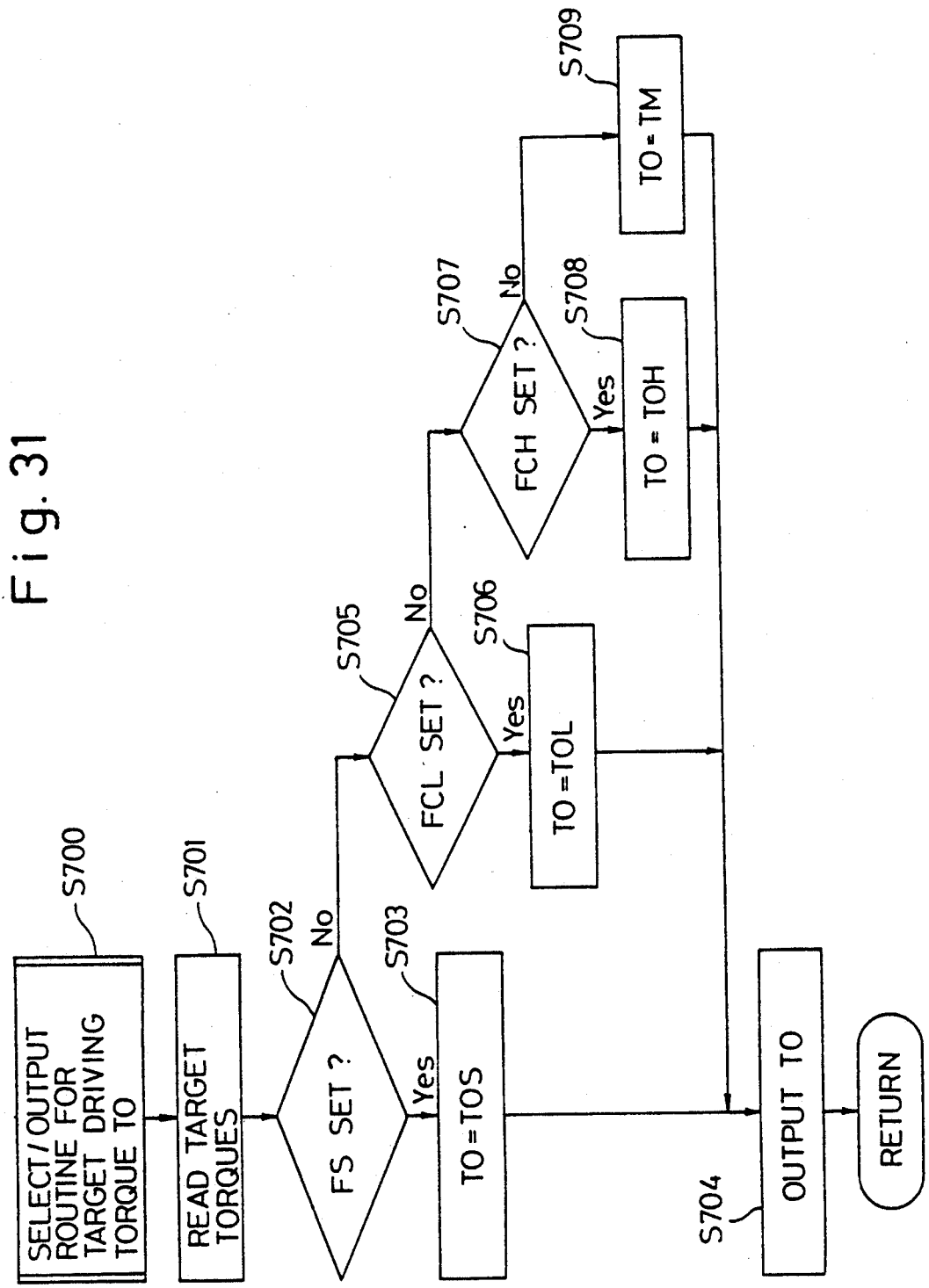
FIG. 31 is a flow chart showing the detail of a select-/output routine for the target driving torque of FIG. 9.

The select/output routine is specifically shown in FIG. 31. Referring now to FIG. 31, therefore, the select/output routine will be described.

Select/Output Routine for Target Driving Torque TO

First, in Step S701, the first to third target torques TOS, TOH and TOL are read individually, and it is then determined in Step S702 whether or not the control flag FS is set. If the result of decision in Step S702 is YES, the first target torque TOS is selected as the target driving torque TO in Step S703. In Step S704, thereafter, the target driving torque TO is delivered from the TCL 112 to the ECU 104. If the result of decision in Step S702 is NO, it is then determined in Step S705 whether or not the control flag FCL is set. If the decision in Step S705 is YES, the third target torque TOL is selected as the target driving torque TO in Step S706. Thereafter, the program proceeds to Step S704, whereupon the target driving torque TO is delivered to the ECU 104.

If the result of decision in Step S705 is NO, on the other hand, it is determined in Step S707 whether or not the control flag FCH is set. If the result of decision in Step S707 is YES, the second target torque TOH is selected as the target driving torque TO in Step S708. Thereafter, the program proceeds to Step S704, whereupon the target driving torque TO is delivered to the ECU 104.

If the decision in Step S707 is also No, then it indicates that none of the first to third manual switches 132, 134 and 136 are on. In these circumstances, therefore, none of the first to third target torques TOS, TOH and TOL are obtained, so that the maximum driving torque TM of the engine 2 is selected as the target driving torque TO in Step S709. Thereafter, the program proceeds to Step S704, whereupon the target driving torque TO is delivered to the ECU 104.

If the low-μ road turning control is required when the third manual switch 136 is not on, an alarm is given to the driver on the spot, as described in connection with the low-μ road decision routine of FIG. 5 and the steering limit decision routine of FIGS. 10 and 11, so that the driver can turn on the third manual switch 136 on delivery of the alarm. Thus, when the low-μ road control is needed, the calculation of the third target torque TOL and the delivery of the target driving torque TO based on the torque TOL can be securely effected.

When the target driving torque TO is supplied from the TCL 112 to the ECU 104, the ECU controls the driving torque of the engine 2 in accordance with the target driving torque TO as follows. The ECU 104 is previously stored with a map for obtaining the throttle opening, with use of the engine speed NE and the driving torque as parameters. Accordingly, the ECU 104 can read out the throttle opening, that is, target throttle opening $\theta TO$, from the target driving torque TO and the engine speed NE. Thereafter, the opening deviation between an actual throttle opening $\theta T$, obtained from the throttle opening sensor 108 (see FIGS. 1 and 2), and a target throttle opening $\theta TO$ is calculated in the ECU 104. When the opening deviation is calculated in this manner, the ECU 104 sets the respective duty factors of the first and second solenoid valves 80 and 94 so as to eliminate the opening deviation, and controls the current supply to the valves 80 and 94 in accordance with the set duty factors. Accordingly, the first and second solenoid valves 80 and 94 drive the throttle lever 18 through the pneumatic actuator 60 in the manner described with reference to FIG. 1, thereby adjusting the actual throttle opening $\theta T$ to the target throttle opening $\theta TO$. As a result, the engine 2 produces a driving torque corresponding to the target throttle opening $\theta TO$. If the maximum driving torque TM of the engine 2 is set as the target driving torque TO, as in Step S709 of FIG. 31, the ECU 104 sets the respective duty factors of the first and second solenoid valves 80 and 94 at predetermined values of the 0% side, so that the engine 2 produces a driving torque corresponding to the depth of depression of the accelerator pedal 44.

When the target driving torque TO is adjusted to the maximum driving torque TM of the engine 2, the respective duty factors of the first and second solenoid valves 80 and 94 at the predetermined values on the 0% side, as described above. Alternatively, however, the duty factors for this case may be controlled so as to be adjusted to the maximum allowable throttle opening of the throttle valve 12, in consideration of the accelerator opening $\theta A$ and the engine speed NE. The maximum allowable throttle opening of the throttle valve, which is set as a function of the engine speed NE, is adjusted to a value in the vicinity of the full-admission opening when the engine speed NE is 2,000 rpm or more, for example. However, it can be reduced to tens of percents of the full-admission opening as the engine speed NE is lowered. Thus, if the accelerator opening $\theta A$ is not greater than the then maximum allowable throttle opening, the engine 2 produces a driving torque corresponding to the depth of depression of the accelerator pedal 44. If the accelerator opening $\theta A$ is greater than the maximum allowable throttle opening, however, the ECU 104 controls the respective duty factors of the first and second solenoid valves 80 and 94 so as to restrict the throttle opening $\theta T$ to the maximum allowable throttle opening. By restricting the throttle opening $\theta T$ in this manner, the responsiveness of reduction control for the driving torque can be improved when the TCL 112 concludes that the driving torque should be reduced. More specifically, the modern policy for vehicle design is intended for the improvement of the acceleration performance and maximum output of the vehicle, so that the passage sectional area of the throttle body 10 tends to be very wide. When the engine 2 is rotating in a low-speed zone, therefore, the intake of the engine 2 will be saturated even if the throttle opening $\theta T$ is only tens of percents of the full-admission opening. Accordingly, the deviation between the target throttle opening $\theta TO$ and the actual throttle opening $\theta T$ of the throttle valve 12, for the point of time when a command for the reduction of the driving torque of the engine 2 is delivered from the TCL 112 through the ECU 104, can be previously made small by restricting the throttle opening $\theta T$ to the maximum allowable throttle opening, instead of making the opening $\theta T$ unconditionally variable in the vicinity of the full-admission opening, depending on the depth of depression of the accelerator pedal 44. Thus, the actual throttle opening $\theta T$ can be quickly adjusted to the target throttle opening $\theta TO$.

In the embodiment described above, whether or not the running road is a low-μ road or whether or not the steering limit capacity is reached is determined by the relationship between actual transverse acceleration GY and the calculated target transverse acceleration GYO. As mentioned before, moreover, the low-μ road decision can be also made on the basis of the relationships between the actual transverse acceleration GY and the predetermined value GYTH and between the stability factor A and the predetermined value AL. A further examination of the graphs of FIGS. 6 and 7 indicates that the friction coefficient of the road or the so-called road-μ can be measured according to the actual transverse acceleration GY. The following is a description of the measurement of the road-μ.

Figure 32:
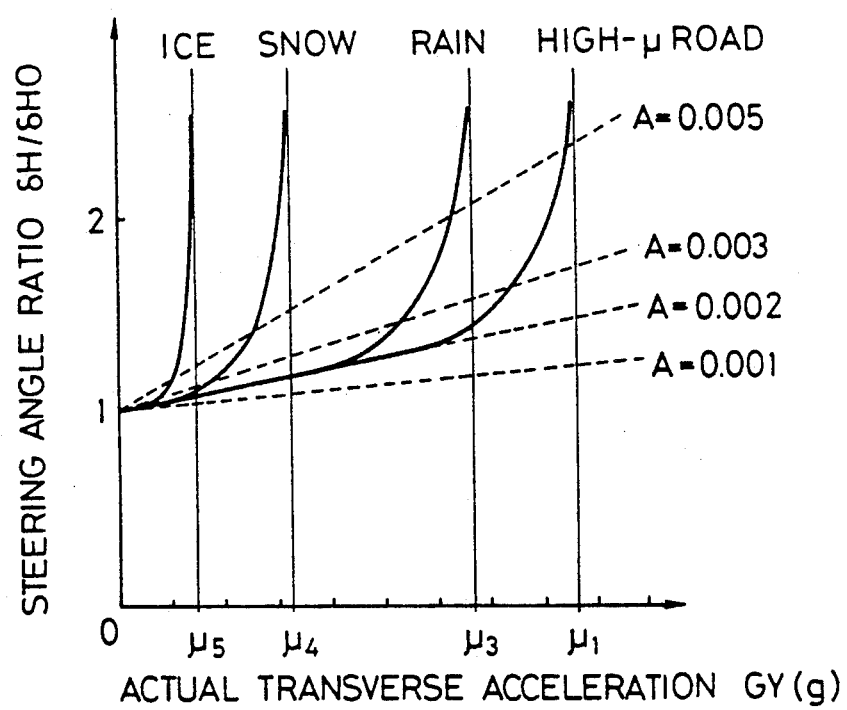
FIG. 32 is a graph showing the relationships between the actual transverse acceleration for various roads and the steering ratio.
Figure 33:
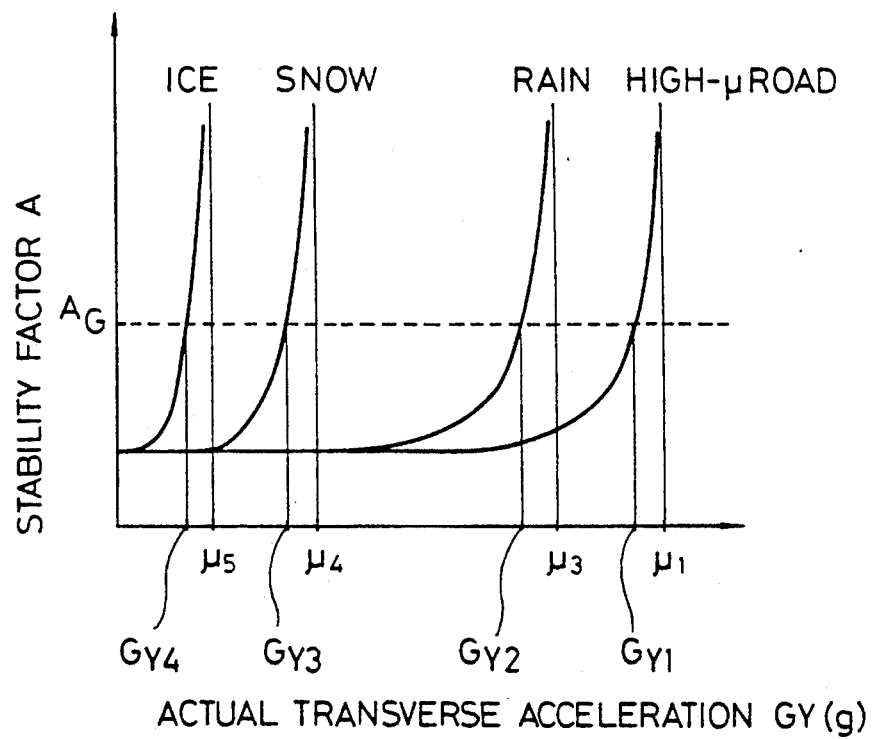
FIG. 33 is a graph similar to FIG. 32, showing the relationships between the transverse acceleration and the stability factor.
Figure 34:
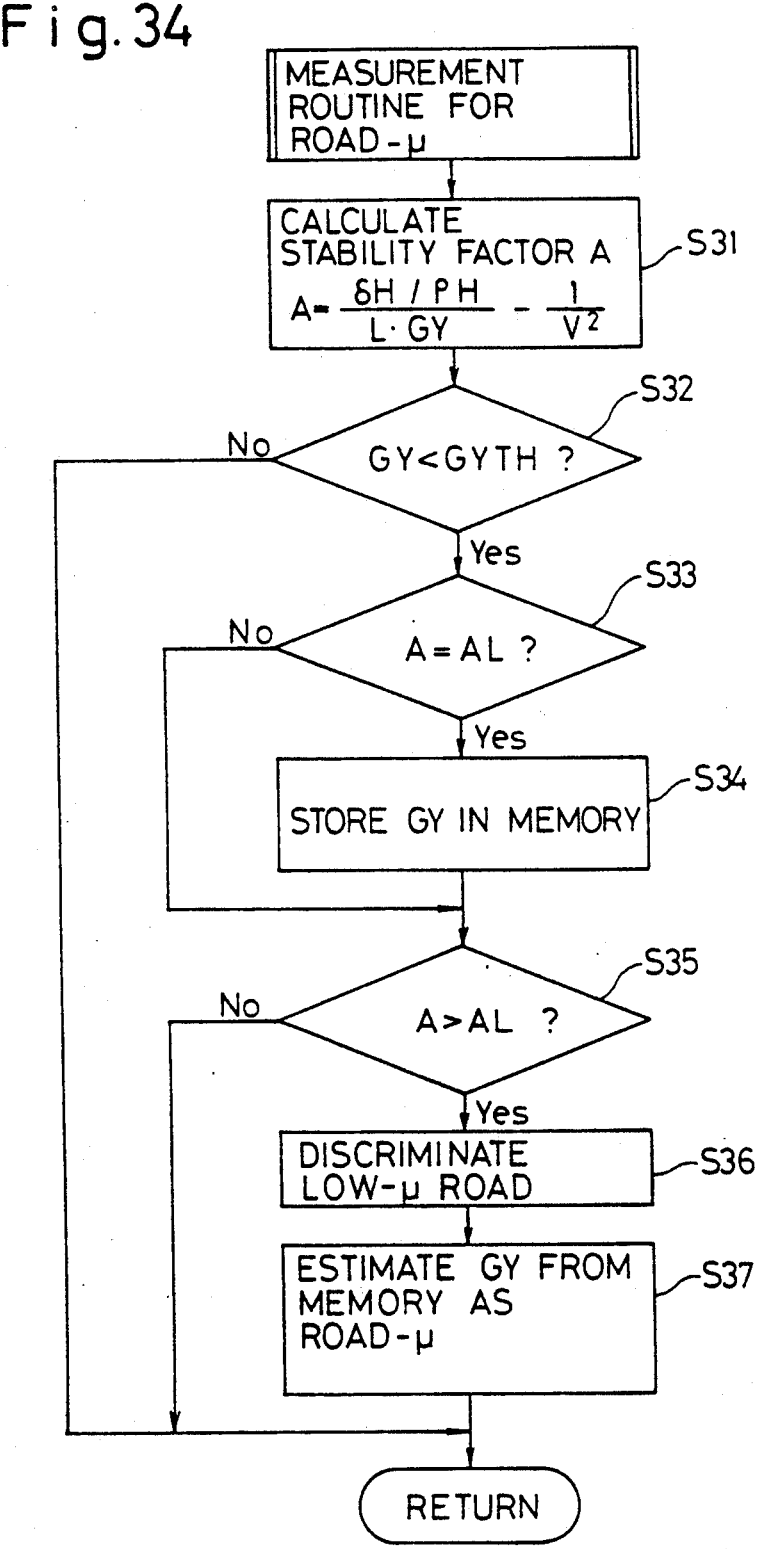
FIG. 34 is a flow chart showing a road-$\mu$ estimation routine.

Referring first to FIGS. 32 and 33, there are shown graphs similar to the graphs of FIGS. 5 and 6. In FIGS. 32 and 33, compared with FIGS. 5 and 6, characteristic curves represent the cases of various types of low-μ roads, individually. In FIG. 32, characteristic curves XL0, XL1, and XL2 represent the cases of an ice-covered road, snow-covered road, and rain-wet road, respectively. In FIGS. 32 and 33, moreover, $\mu1$, $\mu3$, $\mu4$, and $\mu5$ indicate the friction coefficients of a high-μ road, rain-wet road, snow-covered road, and ice-covered road, respectively. If the actual transverse acceleration GY of the vehicle and its corresponding road-μ are numerically compared as aforesaid, therefore, the actual transverse acceleration GY can never exceed the road-μ, as is evident from the characteristic curves XH, XL0, XL1, and XL2 of FIG. 32. If the actual transverse acceleration GY approaches its corresponding road-μ, moreover, the stability factor A drastically increases, as seen from FIG. 33. If the actual transverse acceleration GY (GY1, GY2, GY3, GY4) is detected, for example, when the aforesaid limit value AG is attained by the stability factor A, therefore, the value GY is very approximate to the road-μ ($\mu1$, $\mu3$, $\mu4$, $\mu5$), so that the road-μ can be measured in effect. FIG. 34 shows a measurement routine for the road-μ. Referring now to FIG. 34, the measurement routine executed by means of the TCL 112 will be described.

Road-μ Measurement Routine

First, in Step S31, the stability factor A is calculated according to the same calculation formula used in Step S5 of FIG. 5. In Step S32, it is determined whether or not the actual transverse acceleration GY for the present point of time is smaller than the aforementioned predetermined value GYTH. If the result of decision in Step S32 is NO, Step S33 and its subsequent steps cannot be executed. If the result of decision in Step S32 is YES, however, it is determined in Step S33 whether or not the stability factor A is equal to the limit value AG. If the decision in Step S33 is YES, the present actual transverse acceleration GY is stored in a memory (not shown) of the TCL 112 in Step S34, whereupon the program proceeds to Step S35. If the result of decision in Step S33 is NO, however, the program proceeds directly to Step S35, skipping Step S34. In Step S35, it is determined whether or not the stability factor A is greater than the assumed value AG. If the result of decision in Step S35 is YES, it is concluded in Step S36 that the running road is a low-μ road, as in the case of the low-μ road decision routine of FIG. 5. In Step S37, the value of the actual transverse acceleration GY stored in the memory in Step S34 is estimated as the road-μ. If the result of decision in Step S35 is NO, Steps S36 and S37 cannot be executed. The aforesaid measurement routine is repeatedly executed with a predetermined sampling period, so that the road-μ is continually measured while the vehicle is running. If the result of decision in Step S32 is NO, in the measurement routine of FIG. 34, Step S33 and its subsequent steps cannot be executed, so that the road-μ of a high-μ road cannot be measured.

Figure 35:
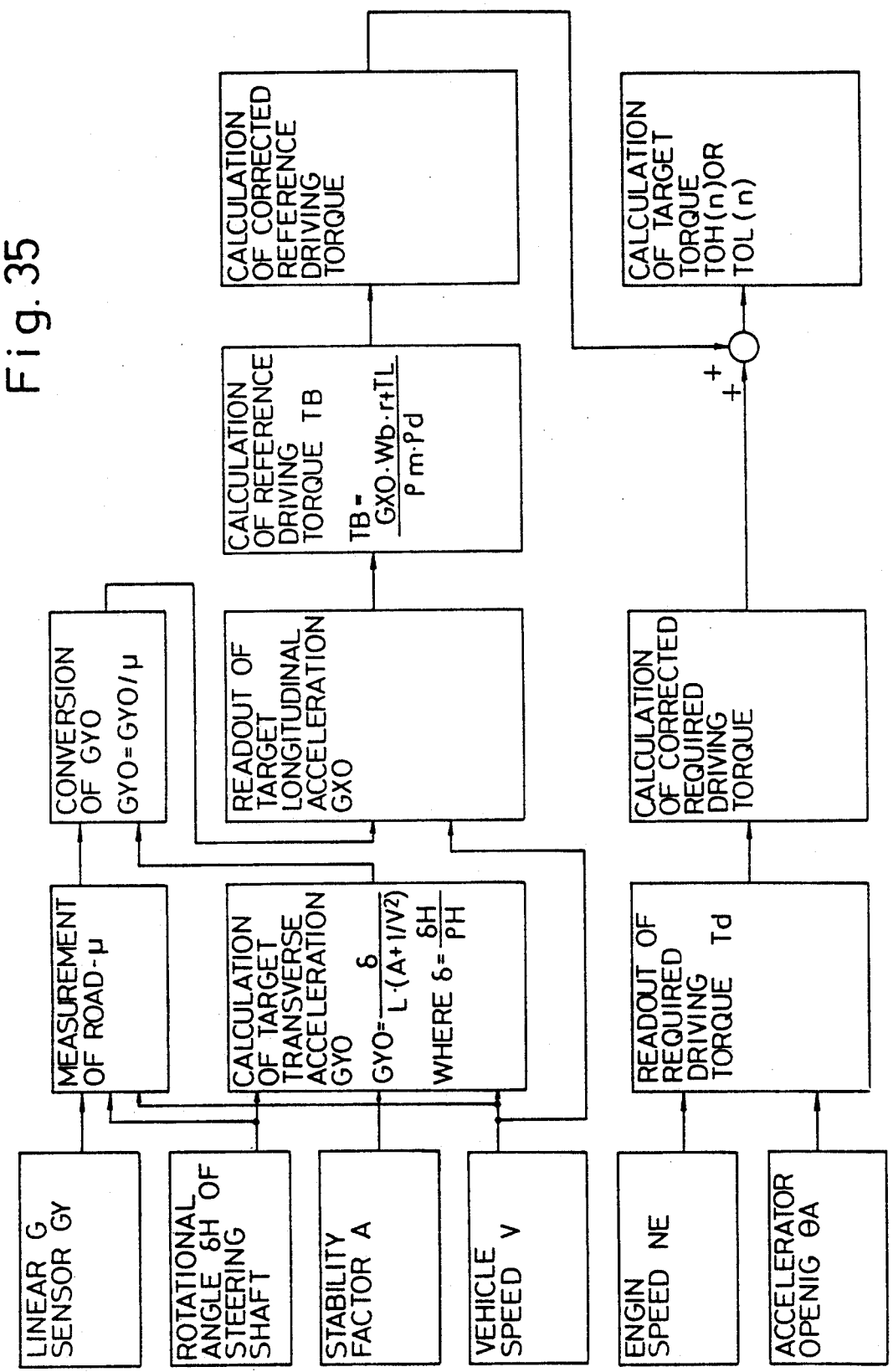
FIG. 35 is a block diagram showing a modification of the block diagrams of FIGS. 19 and 26 for the case where the road-$\mu$ is estimated in the estimation routine of FIG. 34.

If the road-μ of a low-μ road can be measured in this manner, the second and third target torques TOH(n) and TOL(n) can be calculated according to the block diagrams of FIGS. 19 and 26 in consideration of the measured road-μ. More specifically, the second and third target torques TOH(n) and TOL(n) are calculated according to the block diagram of FIG. 35. The target transverse acceleration GYO can be expressed by the following substitution formula using the measured road-μ.

$$GYO = GYO/\mu$$

When the target transverse acceleration GYO is converted according to this equation, the second and third target torques TOH(n) and TOL(n) are calculated in the same manner as aforesaid in accordance with the converted value GYO. In the road-μ measurement routine described above, although the road-μ for a high-μ road is not measured, it may be considered to be 1.

Finally, in executing the output control of the engine while the vehicle is turning, according to the foregoing embodiment, the target torques are calculated individually for high- and low-μ roads. Alternatively, however, a target torque for the case of a road having a friction coefficient intermediate between those of high- and low-μ roads may be also previously calculated so that the final target driving torque TO can be selected among four target torques including the one for the slip control.

Figure 36:
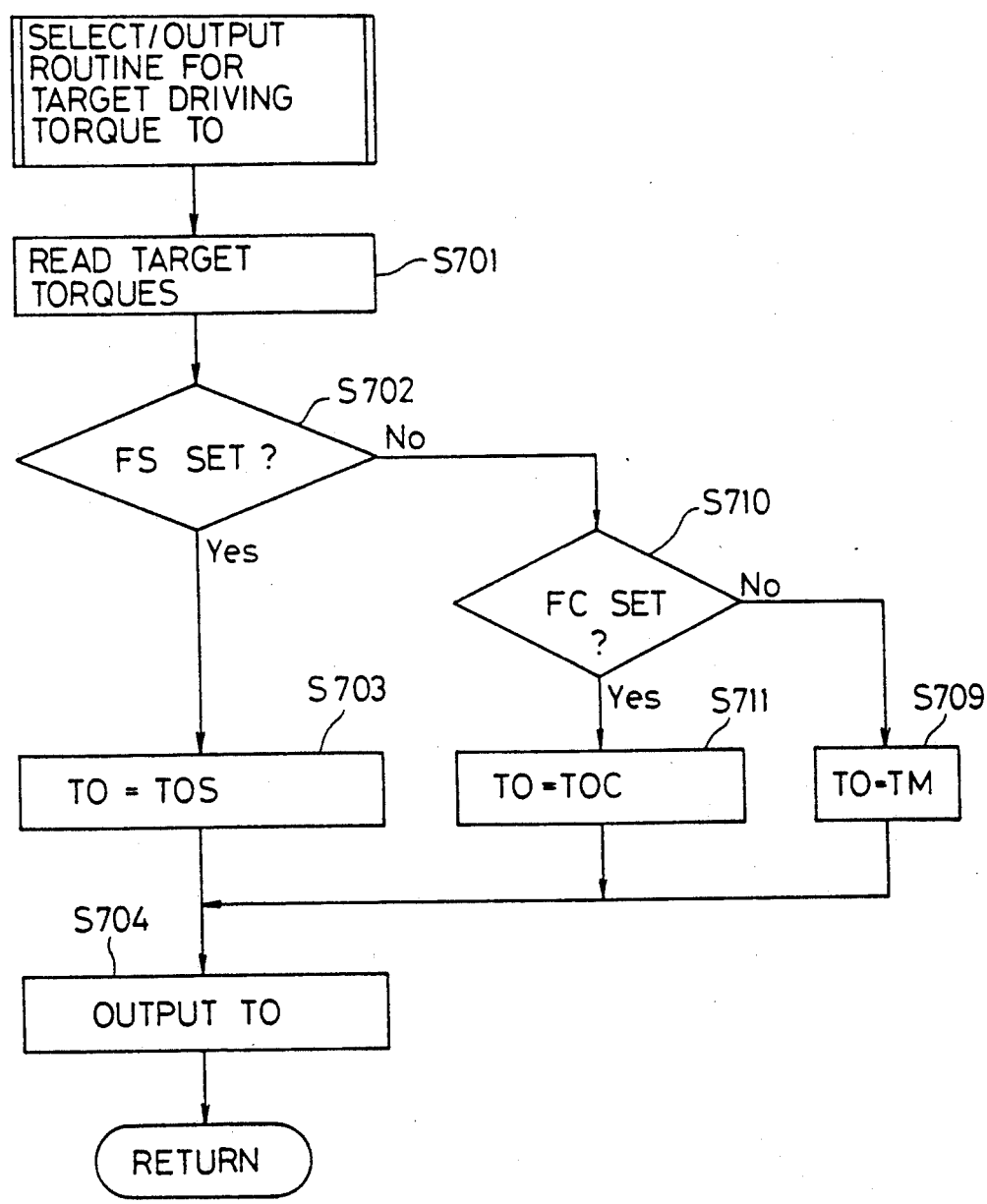
FIG. 36 is a flow chart showing a modification of the routine of FIG. 31.

In executing the turning control, it is necessary only that one target torque TOC for the turning control be calculated without individually calculating the target torques for high- and low-μ roads. FIG. 36 shows the procedure of selection between the target torque TOS for the slip control and the target torque TOC for the turning control, that is, a select/output routine for the target driving torque TO for this case. For the routine of FIG. 36, like reference numerals refer to like steps used in the routine of FIG. 31, and a description of those steps is omitted. In the routine of FIG. 36, Step S710 is executed in place of Steps S705 and S707 in the routine of FIG. 31. In Step S710, it is determined whether or not a control flag FC is set. The flag FC, like the aforementioned control flags FCL and FCH, indicates the turning control being executed. If the result of decision in Step S710 is YES, the target torque TOC is selected as the target driving torque TO in Step S711.

What is claimed is:

1. A device for estimating a friction coefficient of an actual road surface on which a vehicle is running and for regulating a driving condition of said vehicle in accordance with said estimated friction coefficient, said device comprising:

control means for controlling a driving condition of said vehicle;

first detecting means for detecting a running speed of said vehicle;

second detecting means for detecting an actual transverse acceleration acting on said vehicle at substantially a right angle to a running direction of said vehicle;

third detecting means for detecting a steering angle of said vehicle;

calculating means for calculating a stability factor of said vehicle on the basis of said running speed, said actual transverse acceleration, and said steering angle detected by said first, second and third detecting means, respectively, said stability factor being an index indicating a relationship between an increase of said actual transverse acceleration acting on said vehicle and an increase of said steering angle; and first comparing means for comparing said stability factor calculated by said calculating means and a predetermined limit value, and for outputting a first comparison value when said stability factor is greater than said limit value and a second comparison value when said stability factor is smaller than said limit value;

second comparing means for comparing said actual transverse acceleration detected by said second detecting means and a predetermined reference value, and for outputting a third comparison value when said actual transverse acceleration is less than said predetermined reference value and a fourth comparison value when said actual transverse acceleration speed is greater than said predetermined reference value;

estimating means for estimating a friction coefficient of said actual road surface and for determining that when said comparison values output by said first and second comparing means are said first and third comparison values, respectively, said estimated friction coefficient is low as compared said estimated friction coefficient when said comparison values output by said first and second comparing means are not said first and third comparison values, respectively;

said control means controlling said driving condition of said vehicle on the basis of said determination by said estimating means as to whether said estimated friction coefficient of said actual road surface estimated by said estimating means is low.

2. A device according to claim 1, wherein said device further includes means for outputting an alarm signal when said stability factor calculated by said calculating means is greater than said limit value, said alarm signal indicating that said vehicle is in a limit state for steering control.

3. A method for estimating a friction coefficient of an actual road surface on which a vehicle is running and for regulating a driving condition of said vehicle in accordance with said estimated friction coefficient, said method comprising:

a first step of detecting a running speed of vehicle, a steering angle of said vehicle, and an actual transverse acceleration acting on said vehicle at substantially a right angle to the running direction of said vehicle;

a second step of calculating a stability factor of said vehicle on the basis of said running speed, said steering angle, and said actual transverse acceleration detected at said first step, said stability factor being an index indicating a relationship between an increase of said actual transverse acceleration acting on said vehicle and an increase of said steering angle;

a third step of outputting a first comparison value when said stability factor calculated at said second step is greater than a predetermined limit value, outputting a second comparison value when said stability factor calculated at said second step is less than said limit value, outputting a third comparison value when said actual transverse acceleration of said vehicle detected at said first step is less than a predetermined reference value, and outputting a fourth comparison value when said actual transverse acceleration of said vehicle detected at said first step is greater than said reference value;

a fourth step of estimating a friction coefficient of said actual road surface and determining that when said first and third comparison values are output at said third step, said estimated friction coefficient is low, as compared with said estimated friction coefficient of said actual road surface when said comparison values output at said third step are not said first and third comparison values; and a fifth step of controlling a driving condition of said vehicle on the basis of said determination at said fourth step as to whether said estimated friction coefficient of said actual road surface is low.

4. A method according to claim 3, wherein said third step includes outputting an alarm signal when said stability factor calculated at said second step is greater than a predetermined limit value, said alarm signal indicating that said vehicle is in a limit state for steering control.

5. A device for estimating a friction coefficient of an actual road surface on which a vehicle is running and for regulating a driving condition of said vehicle in accordance with said estimated friction coefficient, said device comprising:

control means for controlling a driving condition of said vehicle;

first detecting means for detecting a running speed of said vehicle;

second detecting means for detecting an actual transverse acceleration acting on said vehicle at substantially a right angle to a running direction of said vehicle;

third detecting means for detecting a steering angle of said vehicle;

setting means for setting a target transverse acceleration for said vehicle on the basis of said running speed and said steering angle detected by said first and third detecting means, respectively, and on the basis of an assumption that said vehicle is running on a reference road surface having a predetermined friction coefficient;

comparing means for comparing said target transverse acceleration set by said setting means and said actual transverse acceleration detected by said second detecting means to obtain a comparison value;

estimating means for estimating a friction coefficient of said actual road surface on the basis of the comparison value obtained by said comparing means; and said control means controlling said driving condition of said vehicle on the basis of said estimated friction coefficient of said actual road surface estimated by said estimating means;

said setting means including:

determining means for determining a predetermined stability factor of said vehicle based on the assumption that said vehicle is running on a road surface which has said predetermined friction coefficient, said stability factor being an index indicating a relationship between an increase of said actual transverse acceleration acting on said vehicle and an increase of said steering angle; and means for setting a target transverse acceleration speed of said vehicle on the basis of said stability factor determined by said determining means and on the basis of said running speed and said steering angle detected by said first and third detection means, respectively;

said comparing means including:

means for outputting a first comparison value when said actual transverse acceleration of said vehicle detected by said second detecting means is smaller than said target transverse acceleration set by said setting means; and means for outputting a second comparison value when said actual transverse acceleration of said vehicle detected by said second detecting means is greater than said target transverse acceleration set by said setting means; and said estimating means including means for determining that when said first comparison value is obtained, said estimated friction coefficient of said actual road surface is low as compared with said estimated friction coefficient of said actual road surface when said second comparison value is obtained.

6. A device according to claim 5, wherein said control means includes:

calculating means for calculating a target driving torque for said vehicle on the basis of said target transverse acceleration set by said setting means and said estimated friction coefficient of said actual road surface estimated by said estimating means; and control state means for controlling an actual driving torque of said vehicle according to said calculated target driving torque.

7. A device according to claim 6, wherein:

said calculating means of said control means includes:

first calculating means for calculating a first target driving torque for said vehicle suitable for a road surface having a first friction coefficient on the basis of said target transverse acceleration speed set by said setting means; and second calculating means for calculating a second target driving torque for said vehicle suitable for an actual road surface having a second friction coefficient lower than said first friction coefficient on the basis of said target transverse acceleration speed set by said setting means; and said control state means of said control means includes:

selecting means for selecting one of said first and second target driving torques in accordance with said estimated friction coefficient of said actual road surface estimated by said estimating means.

8. A method for estimating a friction coefficient of an actual road surface on which a vehicle is running and for regulating a driving condition of said vehicle in accordance with said estimated friction coefficient, said method comprising:

a first step of detecting a running speed of said vehicle, a steering angle of said vehicle, and an actual transverse acceleration acting on said vehicle at substantially a right angle to a running direction of said vehicle;

a second step of setting a target transverse acceleration for said vehicle on the basis of said running speed and said steering angle detected at said first step, and on the basis of an assumption that said vehicle is running on a reference road surface having a predetermined friction coefficient;

a third step of comparing said actual transverse acceleration detected at said first step and said target transverse acceleration set at said second step to obtain a comparison value;

a fourth step of estimating a friction coefficient of said actual road surface on the basis of the comparison value obtained at said third step; and a fifth step of controlling a driving condition of said vehicle in accordance with said estimated friction coefficient estimated at said fourth step;

said second step including:

determining a predetermined stability factor of said vehicle based on the assumption that said vehicle is running on a road surface which has said predetermined friction coefficient, said stability factor being an index indicating a relationship between an increase of said actual transverse acceleration acting on said vehicle and an increase of steering angle; and setting a target transverse acceleration for said vehicle on the basis of said determined stability factor and on the basis of said running speed and said steering angle detected at said first step;

said third step including:

outputting a first comparison value when said actual transverse acceleration of said vehicle detected at said first step is smaller than said target transverse acceleration set by said second step; and outputting a second comparison value when said actual transverse acceleration of said vehicle detected at said first step is greater than said target transverse acceleration set at said second step; and said fourth step including:

determining that when said first comparison value is obtained, said estimated friction coefficient of said actual road surface is low, as compared with said estimated friction coefficient of said actual road surface when said second comparison value is obtained.

9. A method according to claim 8, wherein said fifth step includes:

determining a target driving torque for said vehicle on the basis of said target transverse acceleration set at said second step and on the basis of said estimated friction coefficient of said actual road surface estimated at said fourth step, and controlling an actual driving torque of said vehicle according to said determined target driving torque.

10. A method according to claim 8, wherein said fifth step includes:

calculating a first target driving torque for said vehicle suitable for a road surface having a first friction coefficient on the basis of said target transverse acceleration set at said second step;

calculating a second target driving torque for said vehicle suitable for a road surface having a second friction coefficient lower than said first friction coefficient on the basis of said target transverse acceleration set at said second step; and selecting one of said first and second target driving torques in accordance with said estimated friction coefficient of said actual road surface estimated at said fourth step.

* * * * *